United States Patent [19]
Cashman

[11] Patent Number: 5,849,478
[45] Date of Patent: Dec. 15, 1998

[54] BLOCKED-POLYMERASE POLYNUCLEOTIDE IMMUNOASSAY METHOD AND KIT

[76] Inventor: Daniel P. Cashman, 2222 Francisco Dr., Suite 510-121, El Dorado Hills, Calif. 95762

[21] Appl. No.: 996,793

[22] Filed: Dec. 24, 1992

Related U.S. Application Data

[63] Continuation-in-part of Ser. No. 508,259, Apr. 1, 1990, abandoned, Ser. No. 272,648, Nov. 17, 1988, abandoned, and Ser. No. 897,142, Aug. 14, 1986, abandoned.

[51] Int. Cl.[6] .............................. C12Q 1/68; C07H 21/04; G01N 33/53
[52] U.S. Cl. .............................. 435/6; 435/7.1; 435/91.1; 435/91.2; 435/810; 436/501; 536/22.1; 536/23.1; 536/24.1; 536/24.3; 536/24.31; 536/24.32; 536/24.33; 935/78; 935/88
[58] Field of Search ................................. 435/6, 7.1, 810, 435/91, 78, 88, 91.1, 91.2; 436/501; 536/22.1, 23.1, 24.1–24.33

[56] References Cited

U.S. PATENT DOCUMENTS

| | | | |
|---|---|---|---|
| 4,556,643 | 12/1985 | Paau et al. ............................... | 435/501 |
| 4,563,419 | 1/1986 | Ranki et al. .................................. | 435/6 |
| 4,683,195 | 7/1987 | Mullis et al. ................................ | 435/6 |
| 4,767,699 | 8/1988 | Vary et al. ................................... | 435/6 |
| 4,925,785 | 5/1990 | Wang et al. ................................. | 435/6 |
| 4,957,858 | 9/1990 | Chu et al. .................................... | 435/6 |
| 4,994,373 | 2/1991 | Stavrianopoulos et al. ................ | 435/6 |
| 5,168,057 | 12/1992 | Oh et al. ................................... | 435/174 |
| 5,306,619 | 4/1994 | Edwards et al. ............................ | 435/6 |

FOREIGN PATENT DOCUMENTS

0142299A2 5/1985 European Pat. Off. .

OTHER PUBLICATIONS

*Stratogene Catalog* (published 1988 by Stratogene Cloning Systems, La Jolla, CA) p. 26.

Sano, T., et al., "Immuno–PCR: Very Sensitive Antigen Detection by Means of Specific Antibody–DNA Conjugates," Science 258:120–122 (1992).

*Primary Examiner*—W. Gary Jones
*Assistant Examiner*—Ardin H. Marschel

[57] ABSTRACT

An immunoassay method for detecting an analyte in a liquid sample is disclosed. The method includes first contacting the sample with a polynucleotide assay reagent composed of a analyte and an attached polynucleotide containing an initiation region adjacent the site of attachment to the analyte. The sample is reacted with a polymerase and nucleotide triphosphates, to determine the amount of immunocomplex formed between the analyte and the analyte under conditions effective to copy the polynucleotide only if its initiation region is not blocked. The assay mixture is then assayed for the presence of phosphate or pyrophosphate. An immunoassay kit for detecting an analyte in a liquid sample is also disclosed.

10 Claims, 4 Drawing Sheets

BLOCKED-POLYMERASE POLYNUCLEOTIDE IMMUNOASSAY METHOD AND KIT

This application is a continuation-in-part of U.S. patent application Ser. No. 07/508,259, filed Apr. 11, 1990, now abandoned, which is a continuation-in-part of U.S. patent application Ser. No. 07/272,648 filed Nov. 17, 1988, now abandoned which in turn is a continuation-in-part of U.S. patent application Ser. No. 06/897,142 filed Aug. 14, 1986, now abandoned.

FIELD OF THE INVENTION

The present invention relates to a polynucleotide assay reagent, assay methods, and an assay kit utilizing the reagent.

REFERENCES

Barban, S. and R. Goor (1971) J of Virology 7:198.
Brody, R. S. and Frey, P. A. (1981) Biochemistry 20:1245.
Chollet, A. and Kawashima, E. (1985) Nucleic Acids Research 13:1529–1541.
Den Hollander, F. C., et al., J. Immunol. Methods 1972;1:247.
Feinberg and Vogelstein (1983) Anal. Biochem 132:6.
Graham, and Van der Eb, (1973) Virology 52:456.
Hofmann, et al. (1978) J. Am. Chem. Soc. 100:3585.
Johannsson, A., et al, J. Immunological Methods 1986;87:7.
Kempe T., et al. (1982) Nucleic Acids Research 10:6695–6714.
Milstein and Kohler (1975) Nature 256:495.
Ptashne, M., A Genetic Switch: Gene Control and Phage Lambda, Blackwell Scientific (1986).
Rigby et al. (1977) J. Molec. Biol. 113:237.
Saunders, G., et al., J. Clin. Microbiol. 1976;3:604.
Southern, E. (1975) J. Molec. Biol. 98:503.
Towbin, et al., (1979) Proc. Natl. Acad. Sci. USA. 76:4350.
Vosberg, H. P. and Eckstein, F. (1977) Biochemistry 16:3633.
Wannlund, J, et al., Methods in Enzymology 1983;92:426.

BACKGROUND OF THE INVENTION

In biochemistry, clinical chemistry and medicine, analyte binding assay techniques are used for the quantitative and qualitative determination and identification of various materials or substances. One type of binding assay, the immunoassay, in its diverse formats has been especially useful in detecting analytes including viral and bacterial antigens, immunoglobulins, hormones, cell subtypes, pharmaceuticals, toxins and drugs of abuse.

Immunoassay techniques are based upon formation of a complex between antigenic substances and an antibody or antibodies. One of the components of the complex may be labeled permitting complex detection and/or quantitative analysis after separation of the complexed labeled antigen or antibody from an uncomplexed labeled antigen or antibody. There have been many improvements in immunoassays. To maximize sensitivity of detection, amplification systems have been devised ((Saunders, den Hollander).

In a competitive immunoassay format, the antigenic substance in a sample of fluid being tested for its presence competes with a known amount of labeled antigen for a limited quantity of antibody antigen binding sites. The amount of labeled antigen bound to the antibody is inversely proportional to the amount of antigen in the sample.

In an immunometric or non-competitive assay format, the labeled antibody is employed in place of labeled antigen and the amount of labeled antibody associated with an insoluble ternary complex is directly proportional to the quantity of antigenic substance in the fluid sample. The immunometric assay can be used to determine whether the antigen is present in the sample being tested, the washed solid support is tested to detect the presence of labeled antibody. The amount of labeled antibody measured is compared to that for a negative control sample known to be free of the antigen.

Both competitive and immunometric immunoassays can be configured in one of two basic formats: heterogenous and homogenous assays. In a competitive immunoassay, both configurations involve the formation of a reaction mixture comprising a minimum of three reaction components: a known amount of analyte or analyte conjugate, an analyte binding agent, and a sample fluid medium suspected of containing the analyte.

A heterogeneous or two phase assay comprising solid and liquid phases involves immobilization of one member of the analyte/analyte binding agent pair on a solid phase and conjugation of the other to a label or tracer such as an enzyme or radionuclide. The labeled analyte or conjugate competes with analyte suspected to be present in the sample fluid medium for a restricted number of analyte binding sites.

In a homogeneous assay, the separation and preincubation steps are eliminated by measuring the amount of enzyme activity of an analyte-enzyme conjugate rather than the amount of analyte conjugate attached to a support. The presence of an analyte in the sample fluid is established by an increase in activity of the enzyme conjugate (U.S. Pat. Nos. 4,067,774 and 3,817,837).

When either the added analyte conjugate or the sample analyte is bound by the analyte binding agent during an incubation step, the analyte becomes insoluble. The liquid and insoluble phases are then separated and the quantity of analyte in each phase quantitated. The amount of analyte in the sample fluid medium is determined from the quantity of insoluble analyte conjugate following both the incubation and separation steps. Since the amount of bound analyte conjugate is inversely proportional to the quantity of sample analyte, the greater the amount of sample analyte in the sample fluid, the less the amount of analyte conjugate will be present in the insoluble phase (Johannsson, Wannlund).

Heterogeneous assays are commonly used in a diagnostic or a blood bank screening setting not to to measure an individual's prior exposure to a particular infectious agent assuming the individual's immune response was intact at the time of exposure. After exposure to a foreign analyte, such as an infectious agent, an individual makes antibodies to neutralize or otherwise defend against subsequent exposures. Antibodies to an agent often remain with an individual for years after an initial exposure and tests to measure the post exposure antibody responses are categorized as serological testing.

Two well-known formats of serological testing which are performed in a heterogeneous assay format are the ELISA and western blot.

SUMMARY OF THE INVENTION

In one aspect, the invention includes an immunoassay method for detecting an analyte in a liquid sample. The method includes first contacting the sample with binding reagents, including a polynucleotide assay reagent composed of a ligand and a polynucleotide attached to the ligand and containing a initiation region adjacent the ligand, to form an immunocomplex which is present in an amount proportional to the amount of analyte in the sample, and in which the initiation region in the ligand is blocked. The immunocomplex may be formed between the assay reagent and an anti-ligand antibody in the binding reagent, where the sample analyte is a ligand effective to displace the assay reagent from the antibody.

The sample is then reacted with a polymerase and nucleotide triphosphates in a reaction mixture under conditions effective to copy the polynucleotide only if its initiation region is not blocked. Following this, the reaction mixture is assayed for the presence of phosphate or pyrophosphate.

In one general embodiment, the initiation region in the assay reagent includes a selected polynucleotide sequence. The sample is reacted with an oligonucleotide primer which is complementary to said selected initiation region sequence, under conditions effective to anneal the primer to the initiation region only if such is not blocked.

In another general embodiment, the initiation region in the assay reagent includes a promoter region, and the polymerase is capable of copying the polynucleotide after binding to the promoter. The reaction to copy the assay reagent polynucleotide is carried out under conditions in which the polymerase binds to the promoter only if such is not blocked. The polymerase in this embodiment may be a DNA polymerase, DNA-dependent RNA polymerase, reverse transcriptase or replicase.

Also disclosed is an immunoassay kit for detecting an analyte in a liquid sample. The kit includes binding reagents including a polynucleotide assay reagent composed of a ligand and a polynucleotide attached to the ligand and containing a initiation region adjacent the ligand, and effective, in the presence of analyte, to form an immunocomplex which is present in an amount proportional to the amount of analyte in the sample, and in which said initiation region is blocked. Polymerase reagents in the kit are effective to copy the polynucleotide in the assay reagent when the assay reagent initiation region is not blocked. Detection reagents in the kit are designed for detecting the presence of phosphate or pyrophosphate in a reaction mixture.

In one general embodiment, the binding reagent means further includes an analyte-binding molecule, and the ligand in said assay reagent is an analyte-like moiety capable of competing with the analyte for binding to said analyte-binding molecule.

These and other objects and features of the invention will become more fully apparent when the following detailed description of the invention is read in conjunction with the accompanying drawings

DETAILED DESCRIPTION OF THE INVENTION

I. Definitions

Figure 1:
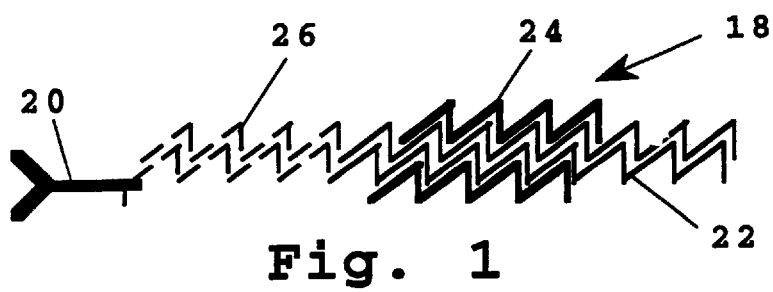
FIG. 1 illustrates general features of one embodiment of a polynucleotide reporter compound formed in accordance with the invention.

A "ligand" refers to any compound capable of binding with high affinity (at least $10^{-6}$M) another compound to form a complex.

An "analyte" refers to compounds whose amount or presence is to be determined in a fluid sample and which is detectable by complex formation with a ligand. Analytes include toxins, drugs of abuse, hormones, pharmaceuticals, nucleic acids, proteins, including immunoglobulins or fragments thereof, or antigenic substances. Analyte also refers to bacteria or viral particles that can react with a ligand immunogenically or otherwise.

An "analyte-binding reagent" refers to a reagent that is capable of binding an analyte in a fluid sample. In some examples, the analyte binding reagent is the ligand of the polynucleotide assay reagent. In other examples the analyte binding reagent is a compound used to attach an analyte to a solid support and which itself is attached to the solid support. The analyte binding reagent may be molecules, such as *Staphylococcus aureus* protein A or Group C Streptococcus Protein G. In further examples the analyte binding reagent is a soluble reagent that can bind an analyte.

An "analyte-like ligand" is a reagent which competes with an analyte for binding to an analyte binding reagent.

A "fluid medium" generally refers to body fluids such as blood, spinal fluid, semen, saliva, effusions, pus, amniotic fluid, urine and the like as well as culture mediums, samples of pharmacological agents, food samples, dairy products, etc. Alternatively fluid mediums can be created from solid materials or pastes by mixing, pulverizing, grinding or otherwise dissolving a solid in a liquid. Fluid samples include fluid obtained from the alveolar air exhaled by a human.

"Polynucleotide" refers to a nucleotide sequence containing at least 20 nucleotides and an initiation region. An "initiation region" refers to a defined sequence necessary for a polymerization/extension agent to begin a polymerization/extension reaction. A polynucleotide containing an initiation region may be double stranded or single stranded.

A "promoter region" refers to a double stranded initiation region. In some cases when the polynucleotide is single stranded a promoter region is formed by annealing an oligonucleotide or primer complementary to the initiation region. The sequence of the bases can be ordered to form special sites, including well-known promoters and operators, as described in Ptashne. These sites are also referred to herein as "initiation sites".

"Immunoassay" refers to an assay where analytes are antigenic substances and ligands are antibodies, fragments thereof, or synthetically prepared antibodies or fragments thereof, which have never seen an antigen, such as those prepared by synthesizing mutations in variable region clones of an antibody of fragment. Alternatively, the analytes are antibodies in a fluid sample and the ligands are substances that bind to the antibody, such as haptens. Immunoassays may be heterogeneous or homogeneous assays.

"Homogeneous assay" refers to an assay in which the presence and/or concentration of analyte is determined without requiring the separation of sample fluid from the reaction components.

"Heterogenous assay" refers to an assay where the reaction medium contains more than one physical phase such as incubating a solid support having reagents attached in a fluid sample. The assay further requires subsequent removal of the sample fluid at a later step in the assay.

"Competitive assay" refers to an assay where the polynucleotide assay reagent has an analyte-like ligand and the reagent competes with the analyte for a known amount of analyte binding reagent.

"Immunocomplex" refers to the complex formed between the polynucleotide assay reagent and a compound with immunological activity capable of binding the polynucleotide assay reagent. In some assays, where the assay reagent binds directly to an immunological analyte, the amount of immunocomplex formed is directly proportional to the amount of analyte in a fluid sample. In competitive assays, where the assay reagent competes with the immunological analyte for binding to a limited known amount of analyte binding reagent, the amount of immunocomplex formed is indirectly proportional to the amount of analyte in a fluid sample.

II. Polynucleotide Assay Reagents for Use in Heterogenous Assays

Heterogenous assay methods for rapidly and accurately detecting analytes in many types of samples including those analyzed by routine clinical laboratories or blood banks are described. The method is preferably an immunoassay method for detecting specific antibodies, such as antibodies against HIV, or specific antigens. Alternatively, the method may be used to detect nonimmunogenic analytes, such as a specific glycoprotein by use of a lectin that recognizes a polysaccharide moiety on such a glycoprotein. The method may also be used to detect HIV by use of the T cell CD4 receptor.

The heterogenous assay method involves binding an analyte to a solid support prior to assaying for the presence of the analyte. The method includes attaching an analyte binding reagent to a solid support. Analyte in a fluid medium then binds to the support by binding interactions with the analyte binding reagent. This is followed by binding of the polynucleotide assay reagent to the immobilized analyte. The amount of immobilized analyte is determined by measuring the amount of assay reagent bound to the support by polymerization reactions.

Polynucleotide assay reagents, analyte binding reagents, solid supports, polymerization reactions, and heterogenous assay methods are described below.

A. Polynucleotide Assay Reagent

The invention relates to a polynucleotide assay reagent for use in quantitative and/or qualitative detection of an analyte in fluid sample. FIG. 1 illustrates general features of one embodiment of the polynucleotide assay reagent. The assay reagent 18 includes a ligand 20, capable of binding with high affinity an analyte, which is linked to a polynucleotide 22, in double stranded or single stranded form, containing an initiation region 24. As illustrated in FIG. 1 the polynucleotide is in double stranded form, and the initiation region is a functional promoter region. The polynucleotide is linked to a ligand moiety indirectly through a linker 26.

The ligand is selected to specifically complex with immunogenic compounds. The ligand may be naturally occurring and be generated biologically or synthetically. Alternatively, the ligand may not be naturally occuring. Synthetically prepared antibodies or fragments thereof, which have never seen an antigen, such as those prepared by synthesizing mutations in variable region clones of an antibody or antibody fragment can be used. Ligands include such molecules as antigenic compounds, the T cell CD4 receptor, antigens, and Fab fragments or antibodies.

Typically, the polynucleotide comprises at least 20 nucleotide residues, each residue comprising a purine or pyrimidine base, a sugar and a phosphate. The residues are usually attached through a phosphodiester linkage. The nucleotides must have at least a minimum of residues ordered in a sequence comprising a initiation region consensus sequence. The polynucleotide may be a double stranded polynucleotide sequence containing a phage promoter, such as the T7 RNA polymerase promoter or the QB phage promoter. Alternatively, the polynucleotide is a single stranded nucleotide sequence containing an initiation region. A functional promoter region is formed by annealing with the initiation region a short oligonucleotide primer to form a functional promoter. In another embodiment the polynucleotide may contain sequences for at least two promoters.

Typically, the polynucleotide is derived from a plasmid having a multiple cloning cassette. The polynucleotide size and the number of promoters can be changed by changing the identity of the insert cloned in the plasmid. Additionally, each nucleotide may have one or more modifications of any of the bases, sugars or phosphates comprising the polymer to prevent polynucleotide degradation.

The linker, or bridging segment links the ligand to the polynucleotide. In accordance with the present invention the bridging segment is selected to not affect the ability of the polynucleotide to function as a substrate for a polymerase or the ability of the ligand to complex an analyte. For example, a biotin/avidin/biotin or avidin/biotin link is suitable as a bridging reagent.

In one embodiment the polynucleotide assay reagent contains a polynucleotide attached to a biotin binding protein, such as avidin, to provide a method for measuring binding of multiple different analytes independently at the same time. Avidin contains four free biotin binding sites to which 4 different biotinylated ligands may bind. Methods of attaching biotin to ligands are well known to those skilled in the art.

The high binding affinity of avidin for biotin results in an interaction that yields a highly sensitive and precise method for simultaneously determining one or more analytes in a fluid medium. Additionally, the use of the biotin bridge permits the use of multiple ligands with unlike affinities toward differing analytes. This advantage is especially useful in screening tests of body fluids for minute quantities of infectious agents or drugs of abuse.

In another embodiment concatamers of the assay reagent may be formed by polymerizing end to end multiple copies of the assay reagent to increase the detection sensitivity of the assay reagent.

B. Analyte Binding Reagents

These analyte binding reagents couple analytes to a solid support. The analyte binding reagents are attached to a solid support by methods known to those skilled in the art without affecting the analyte binding reagent's ability to complex the analyte. Typically, the analyte binding reagent is an immunogenic compound, *Staphylococcus aureus* protein A or Group C Streptococcus protein G. Binding of analyte to the analyte binding reagent does not affect or compete with binding of the assay reagent to an analyte.

C. Solid Supports

Solid supports employed can be made of many materials including filter paper, nylon fibers, plastic beads. Test tubes or microtiter trays composed of polyethylene, polystyrene, polypropylene, or other suitable material can also be used. Other useful solid supports are particulate materials such as agarose, crosslinked dextran or other polysaccharides.

Techniques for attaching ligand binding agents to supports are well known to those skilled in the art. For example, ligand moieties, such as antibodies, may be bound to polysaccharide polymers using the process described in U.S. Pat. No. 3,645,852 or may be bound to a test tube-shaped implement as disclosed in U.S. Pat. No. 4,012,494.

Alternatively, the reagent may be coupled to a solid support suitable for automated analysis of polymerization products.

D. Heterogeneous Assay Format

In some heterogenous assays, the analyte possesses more than two ligand binding sites. Each of these sites is spatially separated from the other to allow for compound binding at both sites. One site allows the analyte to be attached to a solid support. The second site allows for binding of a polynucleotide assay reagent. This allows for formation of a ternary complex is formed between an analyte binding reagent, the analyte and the assay reagent.

Three different methods exist for forming the ternary complex. The analyte binding reagent, the liquid sample suspected to contain an analyte and the reporter reagent can be added simultaneously. In another method, the liquid sample is passed over the solid support prior to addition of the assay reagent. In another method, there is initial reaction of the analyte in a liquid sample with the assay reagent followed by contacting the immunocomplex with solid support.

After ternary complex formation, the liquid medium is removed to wash unbound material. Attachment of the assay reagent to the solid support is then monitored by a polymerization reaction.

The amount of ternary complex is then measured by a polymerization reaction resulting in production of polymerization products, such as phosphate and pyrophosphate. This method illustrates the immunometric assay format where the amount of ternary complex is directly proportional to the amount of analyte in a sample. Examples of immunometric assay methods include ELISA and Western assays.

Alternatively, the heterogenous assay can be used in a competitive assay format. In this type of assay the ligand of the assay reagent is analyte-like. Both analyte and assay reagent compete for a bound analyte-binding reagent. In this case the amount of ternary complex formed which includes the assay reagent is inversely proportional to the amount of analyte in the fluid medium.

In both immunometric and competitive assays of the heterogeneous type the assay reagent may be released from the solid support prior to measuring polymerization products using as substrate the polynucleotide assay reagent that was bound to the support.

E. Assay Reagent Detection by Polymerization Reaction

For polynucleotide assay reagent detection a polymerization reaction is performed using nucleotides modified in the chromophoric ring structure or in the phosphate groups which are suitable substrates for a polymerization agent. For example, the deoxynucleotide analogue, deoxyadenosine-5'-triphosphate-1-(5-sulfonic acid)napthylamidate, (dATP(3) AmN) is used. After a polymerization agent reacts with this deoxynucleotide analogue a fluorescent species will be produced which can be quantitated to determine the number of polynucleotide reporters attached to a solid support.

Polymerization agents include four basic types of polymerases; DNA dependent DNA polymerases, DNA dependent RNA polymerases and RNA/DNA dependent DNA polymerases of retroviruses more commonly known as reverse transcriptase and replicase. RNA polymerases usually require a double-stranded stretch of DNA called a promoter having a template and a non template strand to initiate polymer synthesis. The other two types can utilize a free 3' hydroxyl group of a short oligonucleotide duplex as short as four matching basepairs.

The sensitivity of the polynucleotide assay reagent can be adjusted by use of more than one type of polymerase reaction and/or by the use of more than one promoter. The specific sensitivity requirements of determining a particular analyte or analytes are determined experimentally and necessary adjustments in the ligand binding parameters include polynucleotide length, use of an effector agent which regulates promoter function, such as a repressor protein, the use of one or more promoters and use of one or more polymerase detection reactions, time of incubation, and sample and component dilutions are empirically optimized.

III. Polynucleotide Assay Reagents for Use in Blocked Polymerization Assays

Blocked polymerization assays are typically used in a homogeneous assay format. As described above for heterogenous assays, the blocked polymerization assay is preferably an immunoassay for detecting specific antibodies, such as antibodies against HIV, or specific antigens. Alternatively, the assay method may be used to detect nonimmunogenic analytes, such as a specific glycoprotein by use of a lectin that recognizes a polysaccharride moiety on such a glycoprotein. The method may also be used, for example, to detect HIV by use of the T cell CD4 receptor.

In this method a polynucleotide assay reagent containing a ligand and a polynucleotide sequence with an initiation region in a ligand proximal region is used to detect the presence of an analyte. If an analyte is present in a fluid medium, analyte will bind the assay reagent. When analyte is bound to the polynucleotide assay reagent the analyte blocks the initiation region. Upon addition of a polymerization agent and nucleotides low polymerization activity will be detected because the initiation region is blocked.

If a fluid sample does not contain the analyte, analyte is not present to bind the assay reagent and the initiation region remains unblocked. Upon addition of a polymerization agent and nucleotides high polymerization activity will be detected. Therefore, the presence of an analyte in a fluid medium is associated with a decrease in polymerization activity.

Polynucleotide assay reagents, polymerization reactions, and blocked polymerization assay methods are described below.

A. Polynucleotide Assay Reagents

Figure 2:
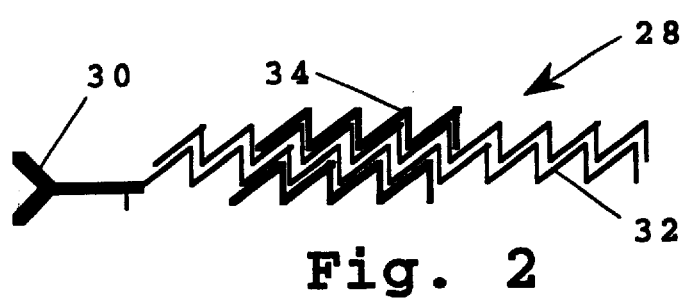
FIG. 2 illustrates general features of another embodiment of a polynucleotide reporter compound formed in accordance with the invention.

The invention relates to a polynucleotide assay reagent for use in quantitative and/or qualitative detection of an analyte in fluid sample. FIG. 2 illustrates general features of another embodiment of the assay reagent 28. The composition includes a ligand 30, capable of binding with high affinity to an analyte, linked to a polynucleotide 32 in double stranded or single stranded form containing an initiation region 34 in the ligand proximal region of the polynucleotide. As illustrated in FIG. 2 the polynucleotide is in double stranded form, and the initiation region is a functional promoter region.

In one embodiment the ligand is selected to specifically complex with an analyte, such as an immunogenic compound. The ligand may be naturally occuring and be generated biologically or synthetically. Alternatively, the ligand may not be naturally occuring. Synthetically prepared antibodies or fragments thereof, which have never seen an antigen, such as those prepared by synthesizing mutations in variable region clones of an antibody of fragment can be used. Ligands include such molecules as antigenic compounds, the T cell CD4 receptor, antigens, and Fab fragments or antibodies. In another embodiment the ligand is analyte-like, so that it will compete with the analyte for binding to an analyte binding reagent.

Typically, the polynucleotide includes at least 20 nucleotide residues, each residue comprising a purine or pyrimidine base, a sugar and a phosphate. The residues are usually attached through a phosphodiester linkage. The nucleotides must have at least a minimum of residues ordered in a sequence forming an initiation region consensus sequence.

In one embodiment the polynucleotide may be a double stranded polynucleotide sequence containing a functional promoter, such as the T7 RNA polymerase promoter or the QB phage promoter. Alternatively, the polynucleotide is a single stranded nucleotide sequence containing an initiation region. A functional promoter region is formed by annealing a short oligonucleotide to a longer polynucleotide leaving a significant portion of the longer polynucleotide in single stranded form.

Each nucleotide may have one or more modifications of any of the bases, sugars or phosphates comprising the polymer to prevent polynucleotide degradation. For example, during polynucleotide synthesis thiophosphodiester bonds between nucleotide sugars can be formed or, alternatively, phosphorothioate oligonucleotides can be ordered from a commercial supplier (Midland Certified Reagent Company). The sulfur atom replaces a non-bridge oxygen on the alpha phosphate. The thiophosphodiester bond is resistant to digestion by nucleases and thus provides protection from any degradation by nucleases present in the sample medium or other components. An alternative method to synthesize thio-substituted polynucleotides is by the use of dNTP(alpha S) nucleotides which are a substrate for DNA polymerase 1 as described (Vosberg, Brody).

Figure 3:
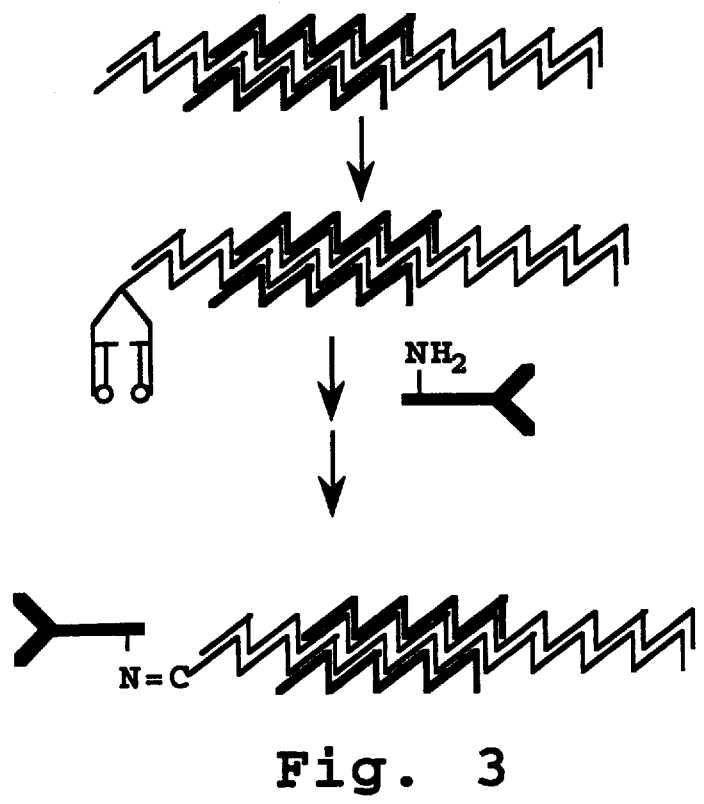
FIG. 3 shows a method of synthesis of a polynucleotide assay reagent with a double stranded section of DNA containing the DNA sequences for at least one promoter.

FIGS. 3 through 7 describe the preparation of specific assay reagents prepared in accordance with the invention. FIG. 3 shows a method of preparing a polynucleotide assay reagent containing a ligand and a double stranded DNA sequence with a promoter in a ligand proximal region of the polynucleotide. As illustrated a diol furanose group is coupled to the 3' end of the polynucleotide that is close to the initiation region. The diol is oxidized to form a dialdehyde which is used to couple a compound containing free amine groups by reductive amination.

Figure 4:
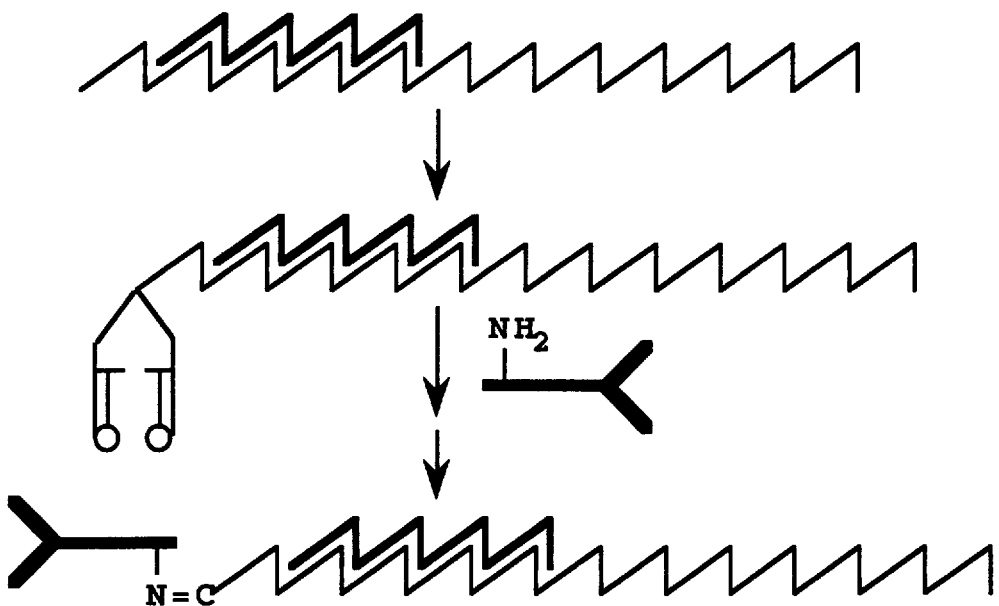
FIG. 4 shows a method of synthesis of a polynucleotide assay reagent with a single stranded section of DNA containing a sequence for at least one strand of a promoter.

FIG. 4 shows a method of preparing a single stranded polynucleotide assay reagent containing a DNA sequence for at least one strand of a promoter including either the template or non-template strand of a RNA phage promoter, such as the T7 phage, attached to a ligand which can serve as a template for a polymerase that will give rise to polymerization products which can be readily detected by conventional techniques.

Figure 5:
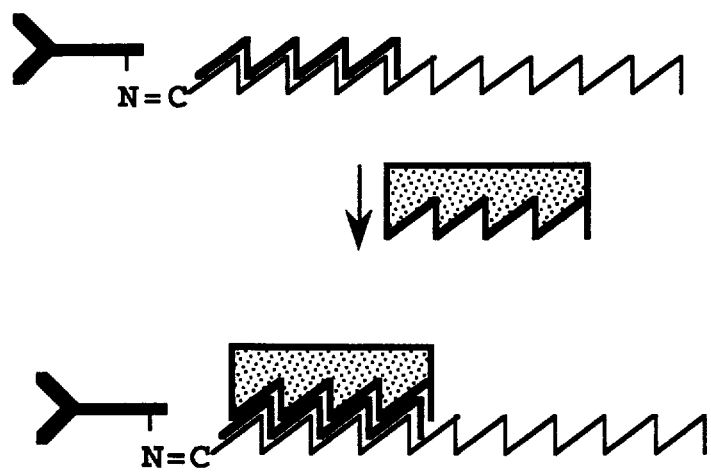
FIG. 5 shows forming a functional promoter by annealing of an oligonucleotide specifically complementary to the transcribed strand of the promoter.

FIG. 5 shows the formation of a functional promoter and nucleic acid template by the annealing of an oligonucleotide specifically complementary to the transcribed strand of the promoter attached to a ligand.

Figure 6:
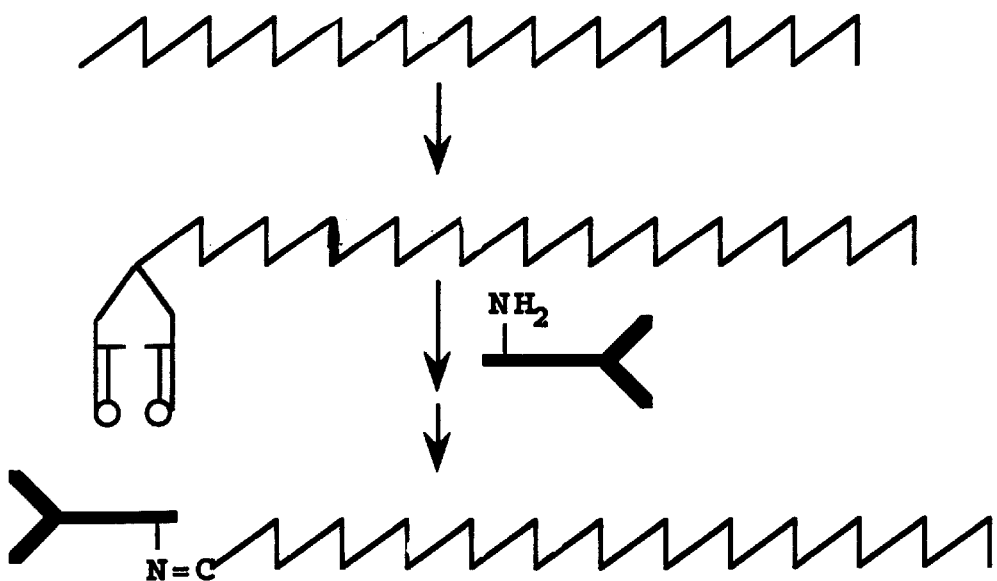
FIG. 6 shows a method of synthesis of a polynucleotide assay reagent with a single stranded section of RNA which can serve as a template for a polymerase.

FIG. 6 shows a method of preparing a single stranded polynucleotide assay reagent containing single stranded RNA attached to a ligand. The reagent serves as a template for a polymerase that will give rise to polymerization products, when an initiation region in the polynucleotide is annealed with a primer.

Figure 7:
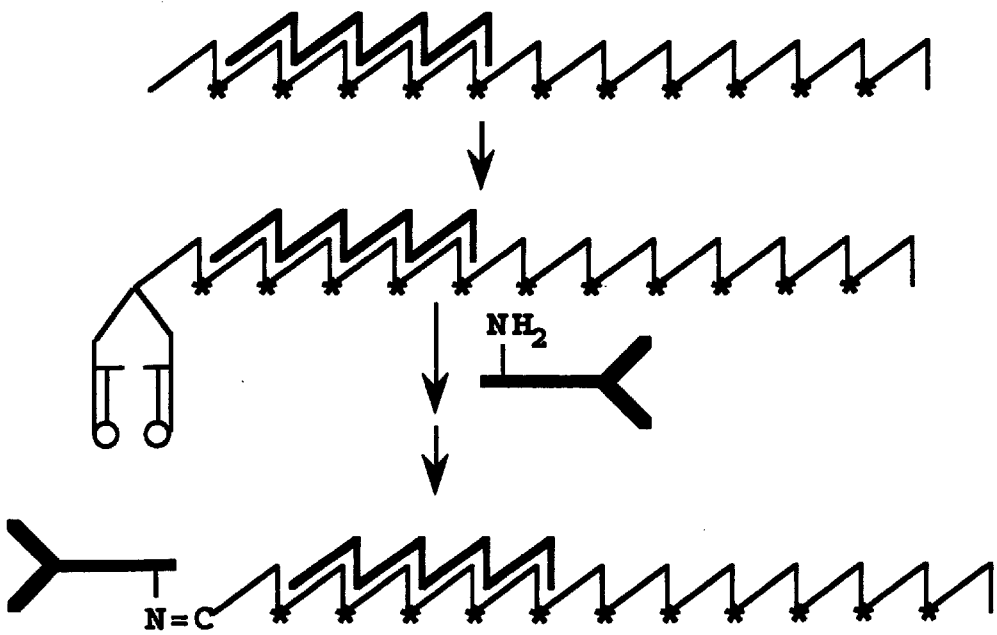
FIG. 7 shows formation of a single stranded heteropolymer DNA or RNA modified (*) so as to withstand exposure to nucleases and which can serve as a substrate or template for a polymerase.

FIG. 7 shows the formation of a single stranded assay reagent with DNA or RNA modified (*) so as to withstand exposure to nucleases and attached to a ligand. The reagent can serve as a substrate or template for a polymerase agent that will give rise to polymerization products which can be readily detected by conventional techniques.

In another embodiment the polynucleotide assay reagent contains a polynucleotide attached to a biotin binding protein, such as avidin, to provide a method for measuring binding of multiple different analytes independently at the same time. Avidin contains four free biotin binding sites to which 4 different biotinylated ligands may bind. Methods of attaching biotin to ligands are well known to those skilled in the art.

In accordance with the present invention, the polynucleotide attached to the ligand serves as a substrate for a polymerization reaction provided that no analyte binds the ligand. Analyte binding blocks binding of a polymerase to the polynucleotide promoter region, and low to no polymerase activity is observed compared to when no analyte is bound to the ligand.

B. Assay Method

A blocked polymerization strategy can be used in both homogenous and heterogenous assays. A preferred embodiment for a homogenous assay method for analyte detection in a fluid sample includes contacting a fluid sample with a polynucleotide assay reagent which complexes with the analyte.

Complex formation between the analyte and assay reagent affects the ability of the template to function as a substrate for a catalytic agent such as a polymerase in a polymerization reaction. One effective way to transmit information about the binding state of the ligand to a catalytic agent, such as a polymerase, is through the use of a promoter. Typically, transcription from a promoter site is inhibited by a protein within 5 angstroms of the promoter region. The present invention takes advantage of the proximity of the ligand-bound analyte to the initiation region inhibiting polymerase activity.

In another embodiment the blocked polymerization assay is a competitive assay where the polynucleotide assay reagent includes an analyte-like ligand which competes with an analyte for a limited amount of analyte binding reagent. Both analyte-like ligand and the analyte bind to the same site(s) of an analyte binding reagent, such that if analyte is bound to the analyte binding reagent, the assay reagent cannot bind. If large amounts of analyte are present in a fluid sample, less assay reagent can bind the analyte binding reagent. Upon addition of a polymerase and nucleotides high levels of polymerization will be obtained. Alternatively, if no or low levels of an analyte are present in a sample, more of the assay reagent will bind to the analyte binding reagent. Upon addition of a polymerase and nucleotides low levels of polymerization will be obtained. In summary, increasing amounts of analyte in a liquid sample increases levels of polymerization from the assay reagent present in the liquid medium.

Figure 8:
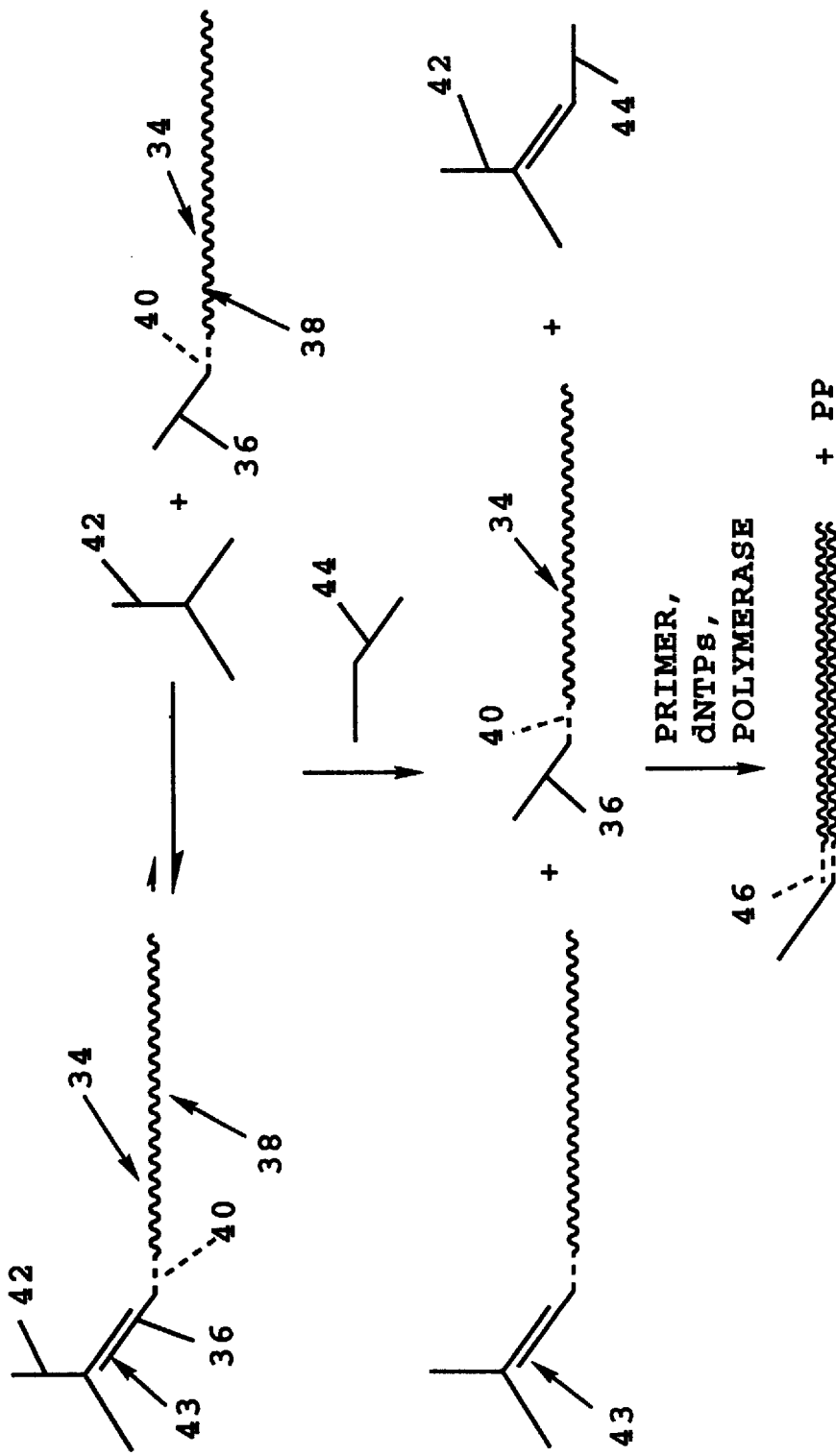
FIG. 8 illustrates on exemplary assay method carried out in accordance with the invention.

A general competitive-assay of the invention is illustrated in FIG. 8. Here the reaction reagents, or reagent means, include an assay reagent 34 composed of an analyte-like ligand 36 and a polynucleotide 38 having a known primer, or initiation sequence 40 (dashed line) immediately adjacent the polynucleotide attachment to the ligand. The reaction reagents also include an anti-ligand antibody 42 which binds the assay reagent with high affinity, as indicated, to form an immunocomplex 43. With the binding of the antibody to the assay reagent, the initiation region in the polynucleotide is blocked, and unable to anneal with a complementary-sequence primer. The antibody and assay reagent are preferably present in approximately equimolar amounts.

When sample with a analyte 44 is added to the reaction reagents, the analyte competes with the assay reagent for binding to antibody, displacing the assay reagent from the immunocomplex 43, as shown in the center frame in FIG. 8, with the amount of displaced (free) assay reagent being proportional—in this case, inversely proportional—to the concentration of analyte in the sample.

The reaction mixture containing the displaced assay reagent is now reacted with a primer 46 under conditions effective to anneal the primer to the complementary-sequence initiation region in the displaced assay reagent. At the same time, primer annealing to the polynucleotide initiation site in immunocomplex 43 is blocked by antibody 42 in the immunocomplex as noted above.

After primer annealing to the free assay reagent, the remainder of the polynucleotide strand is copied in the presence of all four deoxytrinucleotides and a DNA polymerase. The polymerization reaction produces an assay reagent 48 with a double-stranded polynucleotide moiety, with generation of pyrophosphate (PP) as a byproduct.

In the final step of the reaction, the reaction mixture is assayed for pyrophosphate, e.g., by treating the sample with pyrophosphatase and assaying the sample for inorganic phosphate, as detailed below.

The assay method involving a site-specific polymerase is carried out in substantially the same way. Here the initiation site in the assay reagent is a polymerase binding sequence which is blocked by binding an anti-ligand antibody, in an immunocomplex formed between the antibody an assay reagent. With addition of analyte-containing sample, the assay reagent is displaced, in proportion to the concentration of analyte present. The displaced assay reagent is now free to bind the site-specific polymerase, wherein the polynucleotide in the assay reagent is copied, with generation of pyrophosphate.

In another embodiment the assay is a heterogeneous assay. In this assay method the assay reagent is directly coupled to the solid support and can bind an analyte. After contacting the solid support with a fluid medium containing the analyte, the solid support is washed and polymerization reactions are performed to quantitate the amount of immunocomplex formed. Liquid samples have larger quantities of the analyte will have lower levels of the polymerization products.

C. Assay Reagent Detection by Polymerization Reaction

For blocked polymerization reactions the analyte/polynucleotide reagent or analyte binding agent/polynucleotide reagent interactions must continue throughout the entire polymerase detection reaction or valid information regarding the analyte binding state will be forfeited.

Thus, RNA phage polymerase promoters, which function well within the constraints of physiologic buffer concentrations and temperatures, are ideal detection agents. In addition, it is within the intended scope of this invention to exploit nucleic acid modifying enzymes such as a restriction endonuclease or a DNA ligase or novel polypeptides such as gene repressor/analyte binding agent chimeras or activator/analyte binding agent chimeras to allosterically or otherwise transmit information about the binding state of a analyte to the function of a promoter.

Typically, for polynucleotide assay reagent detection a polymerization reaction is performed using nucleotides modified in the chromophoric ring structure or in the phosphate groups can be substrates for a polymerization agent such as a DNA polymerase or RNA polymerase.

After a polymerization agent reacts with this deoxynucleotide analogue a fluorescent species will be produced which can be quantitated to determine the number of polynucleotide reporters attached to a solid support.

There are three basic types of polymerases; DNA dependent DNA polymerases, DNA dependent RNA polymerases and RNA/DNA dependent DNA polymerases of retroviruses more commonly known as reverse transcriptase. RNA polymerases usually require a double stranded stretch of DNA called a promoter having a template and a nontemplate strand to initiate polymer synthesis. The other two types can utilize a free 3' hydroxyl group of a short oligonucleotide duplex as condensed as four matching basepairs.

IV. Immunoassay Kit

In another aspect, the invention includes an immunoassay kit for detecting an analyte in a liquid sample. The kit includes the polynucleotide assay reagent described in Section III containing an initiation region in a region proximal to a ligand. In the presence of an analyte lower polymerization activity is detected because analyte binding to a ligand prevents polymerization by blocking the initiation region.

The kit also contains polymerase reagents effective to copy the polynucleotide in the assay reagent only if its initiation region is not blocked, and detection reagents for detecting the presence of phosphate or pyrophosphate in a reaction mixture.

Alternatively, the ligand is an analyte-like molecule, capable of competing with the analyte for binding to an analyte binding molecule.

In one embodiment the assay reagent includes a selected polynucleotide sequence in the initiation region, and the polymerase reagents include an oligonucleotide which is complementary to the selected initiation region sequence. In another embodiment the assay reagent includes a promoter region, and the polymerase is capable of copying the polynucleotide after binding to the promoter, but only if the initiation region is unblocked.

The kit provides a polymerase which can be either a DNA-dependent DNA polymerase, a DNA-dependent RNA polymerase, a reverse transcriptase or a replicase, and the nucleotide triphosphates include nucleotide triphosphate species which are fluorescence-labeled at the gamma phosphate. The amount of product is determined by measuring fluorescence-labeled phosphate or pyrophosphate.

The following examples illustrate the synthesis of polynucleotide assay reagents and their use in assays to detect an analyte. The examples are intended to illustrate specific ligand tracer polynucleotide compositions and methods of the invention, but are in no way intended to limit the scope of the invention.

Materials

Unless otherwise stated, all reagents can be obtained from Sigma Chemicals or other suppliers of reagent chemicals named in the specification. The terms "tracer nucleic acid" and "template nucleic acid" is used interchangeably with "polynucleotide".

Example 1
Assay Method with Protein G-DNA Polynucleotide Assay Reagent with Functional T7 Promoter In this example a polynucleotide is attached to an analyte, Streptococcus Group C protein G, for use in a heterogeneous assay to detect an analyte, human IgG, specific for the Human Immunodeficiency Virus (HIV).

Preparation of Nucleic Acid with Oxidized Furanose Group

A diol furanose group is coupled to a specific 3' end of a DNA polynucleotide, to reduce the formation of concatamers or polymers between multiple analytes and polynucleotides. Accordingly, a plasmid vector having multiple cloning sites (MCS) and an asymmetric labeling or tailing site is designed to easily facilitate this process.

The commercially available plasmid, pBluescript SK+/- (Stratagene) or other suitable plasmid containing one or more RNA phage promoters is modified by placing the following adapter selectively in the BssH II recognition sequence at site 792 by standard techniques:

5'-CGCGCATGCGGCAGTAGATCTCAC-3' top strand,
3'-GGACGCCGTACTCTAGAGTGGCGC-5' bottom strand.

After completing the construction, this modified vector contains unique Sph I and Bgl II restriction endonuclease sites. Milligram quantities of plasmid DNA are then purified and subjected to the following series of treatments.

One milligram of purified plasmid is completely cleaved to generate approximately 400 pmoles of overhanging 3' ends with Sph I endonuclease, phenol extracted, ethanol precipitated and redissolved in a reaction medium comprised of 250 units of nuclease free terminal transferase enzyme, 2.0 nmoles of rCTP, 2.0 mM $CoCl_2$, 100 mM potassium cacodylate (pH 7.2), 0.2 mM dithiothreitol, heated to 37 degrees C. and incubated for 1 hour. The mixture is phenol extracted, ethanol precipitated and redissolved in a reaction medium comprising 10 mM Tris-HCl (pH7.4), 100 mM NaCl, 10 mM $MgCl_2$, 10 mM 2- mercaptoethanol, 100 ug/ml bovine serum albumin (BSA), 1000 units of Bgl II, heated to 37 degrees C. and incubated for 1 hour. The mixture is phenol extracted, ethanol precipitated, redissolved in aqueous solution, and loaded onto a column of Bio-Gel P-100™ (Bio-Rad Laboratories) preequilibrated with water. The heteropolymer nucleic acid material free of BSA is collected in the void volume, pooled and ready for oxidation by sodium periodate.

Approximately 0.4 nmoles 3' end ribo labeled heteropolymer is dissolved in water and the solution adjusted to pH 7.0 at 0 degrees C. Sodium periodate (0.5 nmoles) is added and the solution is allowed to stand in the dark at 4 degrees C. The reaction is stopped by the addition of ethylenediol (0.05 nmoles) and the reaction is loaded onto a column of Bio-Gel P-30® preequilibrated with water. The oxidized heteropolymer nucleic acids now labeled with a dialdehyde functionality is collected in the void volume, pooled and ready for conjugation with analyte or analyte binding agent. The end product of the treatments is a template nucleic acid with a single dialdehyde functionality with the following linear array of endonuclease sites:

Bgl I T3>>. . . MCS . . . <<T7{vector} Sph I ribodialdehyde. The ribo dialdehyde is located on the template strand of the T7 promoter with the direction of transcription directed away from the dialdehyde group towards the multiple cloning site (MCS) as indicated by the inverse arrows. The length of a T7 transcript from the T7 promoter without any insert in the MCS is about 150 bases in length. The size of a T3 transcript from the T3 promoter without any insert in the MCS is up to about 2900 bases in length. This variability in transcript length, coupled with reverse primers and reverse transcriptase polymerase can be combined with further RNA polymerase reactions to provide a readily amplified detection signal to provide for a wide difference in dynamic ranges.

B. Protein G-DNA Polynucleotide Assay Reagent

The streptococcal Group C protein G can be either directly purified from native sources or is available in a recombinant form modified to improve its function. Protein G binds specifically to the constant region of IgG immunoglobulins with the exception of cat and chicken species and does not bind IgD, IgE or IgM immunoglobulins or serum albumin.

Ten milligrams of modified Protein G (Scripps Laboratories) in 2 ml is dialyzed against 0.125 Nethyl morpholine acetate buffer, pH 8.4, containing 1 mM EDTA until equilibrium. The dialyzed protein G is then reacted with 2.5 mg of terminal aldehyde moiety attached to the oxidized 3' end of heteropolymer template nucleic acid synthesized as described below. The reaction proceeds with gentle mixing for 10 minutes and then sodium borohydride is added in 5 fold excess over aldehyde concentration and the solution is allowed to stand for 35 minutes. The mixture is then applied to a Goat IgG-agarose (Jackson Immunoresearch Labs Inc.) affinity column. The column is washed with 0.07M acetate pH 5.0 buffer and eluted with 0.05 sodium citrate pH approximately 2.8 buffer. The eluted protein G-DNA is dialyzed in TBS (59 mM Tris (pH7.9), 150 mM NaCl) buffer and stored in concentrated form at 4 degrees C. with 0.1% sodium Azide.

C. immobolized HIV Assay Reagent

To 8 grams of nonporous spherical Hydrazide Beads (Pierce) 5 ml of 12.5% glutaraldehyde solution (2.5 ml of 25% glutaraldehyde diluted to 5 ml with 0.1M sodium phosphate, pH 7) is added. The beads are then placed on a rocker with gentle shaking for 2 hours, washed with 200 ml of water in a Buchner funnel followed by a wash with 40 ml of 0.1 sodium phosphate, pH 6.0.

The activated beads are then added to a solution of 5 mg of beta- propiolactone inactivated Human Immunodeficiency Virus (HIV, Scripps Laboratories) which has been dialyzed in 0.1M sodium phosphate, pH 6.0 to equilibrium. After mixing, 2mg of sodium cyanoborohydride is added to the mixture with gentle shaking for 15 hours to reduce Schiff bases. The HIV coupled polystyrene beads are washed with 200 ml of 0.1M sodium phosphate, pH 6.0 followed by a wash with 50 ml of sodium bicarbonate.

The HIV coupled hydrazide beads are added to 10 ml 0.1M sodium bicarbonate containing about 1 mg of sodium borohydride with gentle shaking for 15 minutes. The HIV beads are then washed with 200 ml of sodium carbonate followed by 200 ml of water and then air dried. The air dried HIV coupled beads are then blocked with a 1.0% solution of casein (Sigma C-5890) in phosphate buffered saline for 20 minutes maximum. The beads are then rinsed with 200 ml TBS buffer with 0.1% sodium azide twice, air dried and stored at 4 degrees in a moisture-proof pouch prior to use.

D. Analyte Binding Assay

Into each of at least six tubes is placed 1 HIV bead for assays run in duplicate; two marked as S1 and S2 respectively for sample medium, two marked P1 and P2 for positive control and two marked N1 and N2 for negative control. The beads are washed with TBS and 145 ul of TBS with 10% BSA and either 5 ul of negative control serum, positive control serum or sample serum. The beads are allowed to react for 2 hours with the test/sample fluid and then the beads are washed three times with TBS and 0.5%

Tween-20 (TBST) in order to remove unreacted antibodies. The beads are then treated with a 125 ul of a 1:2000 dilution of the protein G DNA polynucleotide and incubated for 1 hour. The beads are then washed three times with TBST and three times with TBS. The beads are now ready for a polymerase detection reaction.

To each tube is added 100 ul of concentration of transcription/polymerization medium; 40 mM Tris-HCl (pH7.9), 6 mM MgCl$_2$, 2 mM spermidine, 10 mM dithiothreitol (DTT), 0.5 mM each UTP, GTP, CTP, ATP(1)S(3) Amino-naphthalene-5-sulfonate Ester (prepared as directed in Example 10, U.S. patent application 07/483,337 or 07/496971 submitted Feb. 20, 1990 and Mar. 20, 1990, incorporated by reference herein) and 20 units of T7 RNA Polymerase. The samples are mixed in a final volume of 150 ul and the reaction proceeds for 80 minutes at 37 degrees. The samples are then diluted approximately 10 times depending on cuvette volume.

Measurements of fluorescence are made with a fluorimeter such as Perkin-Elmer MPF-44 recording spectrophotometer with correcting spectral attachment with excitation at 360 nm and emission at 500 nm. Cleavage of the alpha-beta phosphoryl bond of ATP(1)S(3)Amino-naphthalene-5-sulfonate Ester produces about a 13 fold increase in fluorescence emission. Samples from the "S" group showing an increase in fluoresence of greater than or equal to 5% relative to the average of the tubes from the "N" group are scored as positive. Samples from "P" group confirm the functioning of the analyte binding assay components. Sensitivity of the assay is limited to measuring an increase of fluorescence of greater than or equal to 5%. With a 0.1 ml reaction volume the production of about 40 pmoles of pyrophosphate-amino-naphthalene-5-sulfonate Ester due to the polymerase/extension agent activity (T7 RNA Polymerase) can be measured. The activity of the RNA Polymerase is proportional to the amount of target/template with low backgrounds provided that conditions for the annealing of the initial primer are stringent.

The exact sample dilutions depend on the length in base pairs of the target insert, the number of nucleotide analogues used or the type of spectrometric detection format employed. For example the detection system can be readily adapted to a microtiter plate format or standard spectrophotometer cuvettes. The use of nucleotide analogues with DNA from prelinearized plasmids used to make the tracer nucleic acids are employed to calibrate the sensitivity of the polymerase/extension detection system. Further investigations with polymerase detection assays at specific dilutions of the analyte binding agent tracer conjugate are useful to establish appropriate dilutions and incubation times of both the sample medium and the analyte binding agent-tracer conjugate as well as optimizing the assay in terms of minimum turn around time, minimum reagent consumption and maximum sensitivity.

Example 2
Assay Method with Goat Antihuman IgG-Single-Stranded DNA Polynucleotide Assay Reagent with a Streptavidin/Biotin Bridge In this example a polynucleotide is indirectly attached through a streptavidin bridge to the analyte, biotin labeled goat antihuman IgG, for use in a heterogeneous assay. The analyte to be detected in an ELISA format as in Example 1, is human IgG specific for HIV.

A. Preparation of Oxidized Single Stranded DNA Polynucleotide The synthesis of ribo/deoxyribose DNA heteropolymers using methylphosphochloridites or methylphosphoamidites is shown by Kempe. Additionally, the 5' phosphate of the heteropolymer is blocked or protected from exonuclease digestion by aminoalkylation with 1,2-diaminoethane (Fluka AG) as described (Chollet). In accord with the above references or other well known techniques the following heteropolymer oligonucleotide is made:

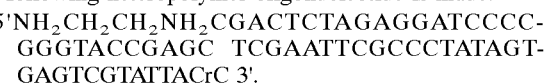

In addition a second oligonucleotide corresponding to the non-template strand of the T7 phage RNA promoter with the following sequence is made:

The single ribose ring (rC) at the 3' end of the purified oligonucleotide is ready for oxidation. Approximately 0.8 nmoles of 3' end ribo-labeled heteropolymer is dissolved in water and the solution adjusted to pH 7.0 at 0 degrees C. Sodium periodate (1.0 nmoles) is added and the solution is allowed to stand in the dark at 4 degrees C. The reaction is stopped by the addition of ethylenediol (0.10 nmoles) and the reaction is loaded onto a column of Bio-Gel P-30™ preequilibrated with water. The oxidized heteropolymer nucleic acids now labeled with a dialdehyde functionality are collected in the void volume, pooled and ready for conjugation with analyte or analyte binding agent. The end product of the treatments is a tracer nucleic acid with a single 3' dialdehyde functionality and the template strand of a T7 RNA phage promoter which direct transcription/polymerization away from the 3' end.

B. Streptavidin Polynucleotide Assay Reagent
Streptavidin is a biotin-binding protein with an approximate molecular weight of 60,000 obtained from Streptomyces avidini which is resistant to proteolytic digestion by trypsin. Twenty milligrams of streptavidin (Scripps Laboratories) in 2 ml of TBS is dialyzed against 0.125 m N-ethyl morpholine acetate buffer, pH 8.4, containing 1 mM EDTA until equilibrium. The dialyzed streptavidin is then reacted with 40 ug of terminal aldehyde moiety attached to the oxidized 3' end of the single stranded heteropolymer tracer DNA synthesized as described below. The reaction proceeds with gentle mixing for 10 minutes and then sodium borohydride is added in 5 fold excess over aldehyde concentration and the solution is allowed to stand for 35 minutes.

The mixture is then dialyzed against 30 mM sodium acetate, (pH 5.0), 50 mM NaCl, 1 mM ZnCl$_2$ and 5% glycerol (v/v) until equilibrium. 100 units of Mung bean nuclease (Stratagene) are added to the medium and incubated for 30 minutes at 30 degrees C. to digest the unreacted nucleic acid. EDTA is added to the medium to make a final concentration of 2 mM and the mixture is then reacted for 30 minutes at 37 degrees with insoluble trypsin attached to polyacrylamide from Bovine Pancreas (Sigma T8386). The immobilized trypsin is separated and the mixture is applied to a Bio-Gel P-100™ column preequilibrated in TBS. The unconjugated streptavidin partitions remains on the column while the streptavidin-tracer nucleic acid conjugate elutes in the void volume and is stored in concentrated form at 4 degrees C. with 0.1% sodium Azide.

C. Analyte Binding Assay
Into each of at least six tubes is placed 1 HIV bead made as described in Example 1. Assays are run in at least duplicate; two marked as S1 and S2 respectively for sample medium, two marked P1 and P2 for positive control and two marked N1 and N2 for negative control. The beads are washed with TBS and 145 ul of TBS with 10% BSA and either 5 ul of negative control serum, positive control serum or sample serum. The beads are allowed to react for 2 hours with the sample/test fluid and then the beads are washed three times with TBS and 0.5% Tween-20 (TBST) in order to remove unreacted antibodies.

The beads are then treated with a 125 ul of 1:2000 dilution of biotin labeled affinity purified goat antibody against human IgG (Zymed, 0.75 mg/ml) and incubated for 1 hour. The HIV beads are then washed three times with TBS and 0.5% Tween-20 (TBST) in order to remove unreacted goat antibodies. A 125 ul volume of a 1:2000 dilution of the stock streptavidin tracer nucleic acid conjugate is added to the separated HIV beads and allowed to react for 20 minutes. The HIV beads are then washed three times with TBST and three times with TBS. The beads are now ready for a polymerase detection reaction.

Unlike the double stranded protein G-tracer nucleic acid conjugate of Example 1, the streptavidin-tracer nucleic acid is single stranded and requires annealing of the non-template strand oligonucleotide, 5' GTAATACGACTCACTAT-AGGGCGAA 3', to create a functional T7 promoter. To the washed beads in each tube is added 145 of concentration of transcription/polymerization medium; 1 nmole of oligonucleotide 5' GTAATACGACTCACTATAGGGCGAA 3', 40 mM Tris-HCl (pH7.9), 6 mM MgCl$_2$, 2 mM spermidine, 10 mM dithiothreitol (DTT), 0.5 mM each UTP, GTP, CTP, ATP(1)S(3)Amino-naphthalene-5-sulfonate Ester (prepared as directed in Example 10, U.S. patent application 07/483, 337 or 07/496,971 submitted Feb. 20, 1990 and Mar. 20, 1990, incorporated by reference herein). The sample is heated to 95 degrees for five minutes and allowed to cool to 37 degrees over 15 minutes. To each tube is added 20 units of T7 RNA Polymerase. The samples are mixed in a final volume of 150 ul and the reaction proceeds for 80 minutes at 37 degrees. The samples are then diluted approximately 10 times depending on cuvette volume and individual results of the assay are interpreted based on fluorescence measurements performed as described in Example 1 above.

Example 3
Assay Method for Detection of One or More Analytes by a Single Polynucleotide Assay Reagent In this example a polynucleotide is attached to Streptococcus Group C protein G for use in a heterogeneous assay to detect one or more different analytes, human IgG specific for the Human Immunodeficiency Virus (HIV) or hepatitis B virus.

A. Immobilized Analyte Binding Reagent

To 8 grams of nonporous spherical Hydrazide Beads (Pierce) 5 ml of 12.5% glutaraldehyde solution (2.5 ml of 25% glutaraldehyde diluted to 5 ml with 0.1M sodium phosphate, pH 7) is added. The beads are then placed on a rocker with gentle shaking for 2 hours, washed with 200 ml of water in a Buchner funnel followed by a wash with 40 ml of 0.1 sodium phosphate, pH 6.0.

The activated beads are then added to a solution of 2.5 mg of beta-propiolactone inactivated HIV, 1.25 mg of Hepatitis B virus (HBV) surface antigen subtype adw and 1.25 mg of Hepatitis B surface antigen subtype ayr (HIV, adw, ayr protein from Scripps Laboratories) which have been dialyzed in 0.1M sodium phosphate, pH 6.0 to equilibrium. After mixing, 2 mg of sodium cyanoborohydride is added to the mixture with gentle shaking for 15 hours to reduce Schiff bases. The HIV coupled polystyrene beads are washed with 200 ml of 0.1M sodium phosphate, pH 6.0 followed by a wash with 50 ml of sodium bicarbonate.

The HBV/HIV coupled hydrazide beads are added to 10 ml 0.1M sodium bicarbonate containing about 1 mg of sodium borohydride with gentle shaking for 15 minutes. The HBV/HIV beads are then washed with 200 ml of sodium carbonate followed by 200 ml of water and then air dried. The air dried HIV coupled beads are then blocked with a 1.0% solution of casein (Sigma C-5890) in phosphate buffered saline for 20 minutes maximum. The beads are then rinsed with 200 ml TBS buffer with 0.1% sodium azide twice, air dried and stored at 4 degrees in a moisture proof pouch prior to use.

B. Analyte Binding Assay

Into each of at least six tubes is placed 1 HBV/HIV bead for assays run in at least duplicate; two marked as S1 and S2 respectively for sample medium, two marked P1 and P2 for positive control and two marked N1 and N2 for negative control. The ELISA type assay is run identically and positive results are recorded as described in Example 1. Interpretation of a positive test is limited in that it determines whether one or both types of immunoglobulin analytes are present in the sample medium. Although this not necessarily as informative as running two separate assays, immobilizing more than one type of analyte binding agent on a single support reduces labor and reagent expenses. In triage types of testing, such as screening blood products, this limited amount of information is adequate to make the necessary medical decisions regarding processing of donor specimens.

Example 4
Assay Method with Goat F(ab')$^2$-Polynucleotide Assay Reagent

In this example a polynucleotide is directly attached to a analyte, a goat F(ab')$_2$ fragment reactive with human IgG, for use in a heterogeneous analyte binding assay. The analyte to be detected in an ELISA format as in Example 2, is human IgG specific for HIV.

A. F(ab')$_2$ Fragment Polynucleotide Assay Reagent

Treatment of IgG immunoglobulin with pepsin cleaves it into two functional fractions, a F(ab')$_2$ domain which bonds antigen, and the Fc region which mediates effector functions such as complement fixation, monocyte binding and placental transmission. Ten milligrams of affinity purified plain unconjugated goat F(ab')$_2$ directed against human IgG (Boehringer Mannheim Biochemicals) in 2 ml is dialyzed against 0.125 N-ethyl morpholine acetate buffer, pH 8.4, containing 1 mM EDTA until equilibrium.

The dialyzed goat F(ab')$_2$ is then reacted with 40 ug of terminal aldehyde moiety attached to the oxidized 3' end of the single stranded heteropolymer tracer DNA synthesized as described in Example 2. The reaction proceeds with gentle mixing for 10 minutes and then sodium borohydride is added in 5 fold excess over aldehyde concentration and the solution is allowed to stand for 35 minutes.

The mixture is then applied to a Bio-Gel P-300® column preequilibrated in TBS. The goat F(ab')$_2$-polynucleotide reagent elutes as the first peak of the gel filtration column. The fractions are pooled and stored in concentrated form at 4 degrees C. with 0.1% sodium Azide.

B. Analyte Binding Assay

Into each of at least six tubes is placed 1 HIV bead made as directed in Example 1 for assays run in at least duplicate; two marked as S1 and S2 respectively for sample medium, two marked P1 and P2 for positive control and two marked N1 and N2 for negative control. The ELISA type assay is run similar to Example 2 above except with fewer steps. The beads are washed with TBS and 145 ul of TBS with 10% BSA and either 5 ul of negative control serum, positive control serum or sample serum. The beads are allowed to react for 2 hours with the sample/test fluid and then the beads are washed three times with TBS and 0.5% Tween-20 (TBST) in order to remove unreacted antibodies.

The beads are then treated with a 125 ul of 1:2000 dilution of affinity purified goat F(ab')$_2$nucleic acid conjugate and incubated for 1 hour. The HIV beads are then washed three times with TBS and 0.5% Tween-20 (TBST) followed by three washes with TBS unreacted goat F(ab')₂-nucleic acid conjugate. The beads are now ready for a polymerase detection reaction. The polymerase detection reaction is run and interpreted as shown in Example 2.

Example 5
Assay Method with Goat Antihuman IgG-Single Stranded DNA Polynucleotide Assay Reagent with a Biotin/Streptavidin/Biotin Bridge In this example a polynucleotide is indirectly attached through a biotin/streptavidin/biotin bridge to goat antihuman IgG for use in a heterogeneous analyte binding assay. The analyte to be detected in an ELISA format is human IgG specific for HIV.

A. Preparation of Biotin Labeled DNA

The commercially available plasmid, pBluescript SK+/− (Stratagene) modified with a Sph I/Bgl II adapted as described in Example 1 or other suitable plasmid containing one or more RNA phage promoters is constructed. Milligram quantities of plasmid DNA are then purified and subjected to the following series of treatments. One milligram of purified plasmid is completely cleaved to generate approximately 400 pmoles of overhanging 3' ends with Sph I endonuclease, phenol extracted, ethanol precipitated. It is redissolved in a reaction medium comprising 250 units of nuclease free terminal transferase enzyme, 2.0 nmoles of 5-([N-biotinyl]-3-amino-allyl)-2'-deoxyuridine 5'triphosphate, 2.0 mM CoCl₂, 100 mM potassium cacodylate (pH 7.2), 0.2 mM dithiothreitol, heated to 37 degrees C. and incubated for 1 hour. 5-([N-biotinyl]-3-amino-allyl)-2'-deoxyuridine 5'-triphosphate is a competitive inhibitor of terminal transferase and results in the addition of 1 to 2 biotin labeled oligonucleotides per nucleic acid strand.

The mixture is phenol extracted, ethanol precipitated and redissolved in a reaction medium comprising 10 mM Tris-HCl (pH7.4),100 mM NaCl, 10 mM MgCl₂, 10 mM 2-mercaptoethanol, 100 ug/ml bovine serum albumin (BSA), 1000 units of Bgl II, heated to 37 degrees C. and incubated for 1 hour. The mixture is phenol extracted, ethanol precipitated, redissolved in aqueous solution, and loaded onto a column of Bio-Gel P-100™ preequilibrated with water. The heteropolymer nucleic acids free of BSA are collected in the void volume, pooled and ready for use in analyte binding assay.

B. Streptavidin/Biotin Polynucleotide

In TBS buffer with 0.1% sodium azide are combined 0.4 nmoles of streptavidin and 0.4 nmoles of tracer nucleic acid biotinylated with up to two biotin labeled nucleotides at a single end. The mixture is allowed to react for 30 minutes and then stored in concentrated form at 4 degrees C. until use.

C. Analyte Binding Assay

The analyte binding assay overall is similar to that described in Example 2 above with two exceptions; 1) a streptavidin/biotin tracer nucleic acid conjugate is employed instead of the streptavidintracer nucleic acid and 2) the biotin tracer nucleic acid is double stranded and does not require the annealing of a non-template strand to create a functional promoter.

Into each of at least six tubes is placed 1 HIV bead made as described in Example 1. Assays are run in at least duplicate; two marked as S1 and S2 respectively for sample medium, two marked P1 and P2 for positive control and two marked N1 and N2 for negative control. The beads are washed with TBS and 145 ul of TBS with 10% BSA and either 5 ul of negative control serum, positive control serum or sample serum. The beads are allowed to react for 2 hours with the sample/test fluid and then the beads are washed three times with TBS and 0.5% Tween-20 (TBST) in order to remove unreacted antibodies.

The beads are then treated with a 125 ul of 1:2000 dilution of biotin labeled affinity purified goat antibody against human IgG (Zymed, 0.75 mg/ml) and incubated for 1 hour. The HIV beads are then washed three times with TBS and 0.5% Tween-20 (TBST) in order to remove unreacted goat antibodies. A 125 ul volume of a 1:2000 dilution of the stock streptavidin/biotin tracer nucleic acid conjugate is added to the separated HIV beads and allowed to react for 20 minutes. The HIV beads are then washed three times with TBST and three times with TBS. The beads are now ready for a polymerase detection reaction.

Since the streptavidin/biotin tracer polynucleotide is double stranded, the polymerase detection assay can be run and interpreted exactly is shown in Example 1 above. In addition, if increased sensitivity and/or assay speed is desired, the biotinylated tracer nucleic acid can be titrated with streptavidin at a stoichiometry of 3 nucleic acid strands to 1 streptavidin.

Example 6
Assay Method with an Immobilized Analyte-Binding Reagent and Protein G-Polynucleotide Assay Reagent In this example a polynucleotide is attached to Streptococcus Group C protein G for use in a heterogeneous analyte binding assay to detect an analyte, human IgG specific for particular structural proteins of the HIV.

A. Preparation of First Analyte Binding Agent Immobilized to a Membrane

Western blot analysis is performed by the electrophoresis of 10 ug/well equivalent of HIV (Scripps Laboratories) on a 12% polyacrylamide slab gel in the presence of sodium dodecylsulfate (SDS). The protein material is electrophoretically transferred to a nitrocellulose sheet, as described (Towbin). After transfer the sheet is air dried and then is incubated with 1.0% Casein solution in TBS for 30 minutes. The sheet is then rinsed in TBS with 0.1% sodium azide and cut into 0.5 cm strips cut so as to provide representative proteins of HIV from each of the following sizes; p18, p24, p31, gp41, p51, p55, p65, gp120 and gp160. The strips are dried and stored desiccated until ready for use.

B. Analyte Binding

Into each of at least six tubes is placed 1 HIV strip for assays run in at least duplicate; two marked as S1 and S2 respectively for sample medium, two marked P1 and P2 for positive control and two marked N1 and N2 for negative control. The HIV strips are washed with TBS and 145 ul of TBS with 10% BSA and either 5 ul of negative control serum control, positive control serum or sample serum. The HIV strips are allowed to react for 2 hours with the test/sample fluid and then the HIV strips are washed three times with TBS and 0.5% Tween-20 (TBST) in order to remove unreacted antibodies. The HIV strips are then treated with a 125 ul of a 1:2000 dilution of the protein G tracer nucleic acid conjugated and incubated for 1 hour. The HIV strips are then washed three times with TBST and three times with TBS. The beads are now ready for a polymerase detection reaction.

After reacting with a polymerase the nucleotide analogue, ATP(3)Napthol Ester, (prepared as directed in Example 28 in U.S. patent application 07/483,337 or 07/496,971 submitted Feb. 20, 1990 and Mar. 20, 1990 respectively) a directly observable insoluble product, is formed on the support matrix in the presence of alkaline phosphatase. A nucleotide analogue capable of producing a colored precipitate is necessary for analyte assays with format that requires directly observing an insoluble product such as a western, southern or northern blots.

To each tube is added 100 ul of concentration of transcription/polymerization medium; 40 mM Tris-HCl (pH7.9), 6 mM $MgCl_2$, 2 mM spermidine, 10 mM dithiothretiol (DTT), 0.5 mM each UTP, GTP, CTP, ATP(3) Naphtol Ester (prepared as directed in Example 28, U.S. patent application 07/483,337 or 07/496,971 submitted Feb. 20, 1990 and Mar. 20, 1990, incorporated by reference herein) and 20 units of T7 RNA Polymerase. The samples are mixed in a final volume of 150 ul and the reaction proceeds for 80 minutes at 37 degrees. Ten units of alkaline phosphatase and 5 nmoles of $ZnCl_2$ obtainable from Sigma Chemical Co. are added to each tube. To each sample is added 10 ul of freshly prepared diazonium salt, usually Fast Red TR (5 mg/ml in 0.1M TrisHCl buffer pH 9. The samples are incubated for up to 60 minutes at 30 degrees.

The samples are then evaluated by direct observation for the presence of precipitate. For a permanent record a camera with Polaroid® 612 film (Sigma) is placed on top of the flat strip while the plate is marked to preserve the orientation of the individual proteins. The cleavage of the alpha-beta phosphoryl bond of ATP(3)Napthyl Ester as a result of the nucleotide analogue reacting with the polymerase/extension agent produces a pyrophosphate ester. An insoluble precipitate is generated by removal of the pyrophosphate group with alkaline phosphatase or other nuclease and reaction of the napthol group with a diazonium salt. Different colored precipitates can be produced depending on the type of diazonium salt employed.

Unlike the pyrophosphate ester, the nucleotide(3)Napthol Esters are not substrates for alkaline phosphatase. The diazonium reagent treatment is calibrated so that a colored precipitate and a substantially clear supernatent are produced. The amount of insoluble material produced, assuming the presence of adequate alkaline phosphatase and diazonium reagent, is proportional to the presence of the analyte as determined by the activity of the polymerization/extension agent.

Samples from the "S" group showing an increase in the visually observable precipitate relative to a negative control, "N" group are scored as positive. Sensitivity of the assay is limited to measuring an increase of precipitate relative to the blank control. With a 0.05 ml reaction volume the production of about 40 nmoles of pyrophosphate- aminonaphthalene-5-sulfonate Ester due to the polymerase/extension agent activity (T7 RNA Polymerase) can be measured. The activity of the RNA Polymerase is proportional to the amount of analyte present in the initial sample fluid. Low backgrounds are ensured when the conditions for the binding of the initial analyte are specific and reagents are present in adequate amounts. Samples from "P" group confirm the functioning of the ligand binding assay components.

Example 7

Assay Method with an Immobilized Analyte-Binding Reagent and Biotin Rat Monoclonal Anti-HIV Assay Reagent In this example an assay reagent is indirectly attached to an analyte binding reagent through a biotin/streptavidin bridge for use in a heterogeneous analyte binding assay to detect an analyte, such as an HIV particle.

A. Biotin Rat Monoclonal Anti-HIV Conjugate

A rat monoclonal antibody (Zymed) that reacts with HIV strains LAV, ARV and HTLV III is dialyzed in 0.1M bicarbonate buffer, pH 8.4 at a concentration of 10 mg/ml. Biotin-N-Hydroxysuccinimide (BNHS) is dissolved at a concentration of 10 mg/ml in dimethylformamide immediately before use. The dissolved BNHS is added to the dialyzed protein solution at a ratio of 1:10 (BHNS/protein, w/w) while slowly mixing. The mixture is incubated for 1 hour at room temperature and then dialyzed extensively in TBS. The concentrated biotin labeled rat anti-HIV immunoglobulin is stored at 4 degrees C.

B. Immobilized First Analyte Binding Agent

To 8 grams of nonporous spherical Hydrazide Beads (Pierce) 5 ml of 12.5% glutaraldehyde solution (2.5 ml of 25% glutaraldehyde diluted to 5 ml with 0.1M sodium phosphate, pH 7) is added. The beads are then placed on a rocker with gentle shaking for 2 hours, washed with 200 ml of water in a Buchner funnel followed by a wash with 40 ml of 0.1 sodium phosphate, pH 6.0.

The activated beads are then added to a solution of 5 mg of affinity purified polyclonal human IgG. Human IgG is purified by affinity chromatography using HIV as an absorbent from HIV plasma (Scripps Laboratories) and is dialyzed against 0.1M sodium phosphate, pH 6.0 until equilibrium. After mixing, 2 mg of sodium cyanoborohydride is added to the mixture with gentle shaking for 15 hours to reduce Schiff bases. The HIV binding coupled polystyrene beads are washed with 200 ml of 0.1M sodium phosphate, pH 6.0 followed by a wash with 50 ml of sodium bicarbonate.

To the HIV binding hydrazide beads is added 10 ml 0.1M sodium bicarbonate containing about 1 mg of sodium borohydride with gentle shaking for 15 minutes. The HIV binding beads are then washed with 200 ml of sodium carbonate followed by 200 ml of water and then air-dried. The air-dried HIV binding coupled beads are then blocked with a 1.0% solution of casein (Sigma C-5890) in phosphate buffered saline for 20 minutes maximum. The beads are then rinsed with 200 ml TBS buffer with 0.1% sodium azide twice, air dried and stored at 4 degrees in a moisture-proof pouch prior to use.

C. Streptavidin/Biotin Conjugated Tracer Nucleic Acid

In TBS buffer with 0.1% sodium azide are combined 0.4 nmoles of streptavidin and 1.2 nmoles of tracer nucleic acid biotinylated at with up to two biotin labeled nucleotides at a single end made as directed in Example 5 above. The mixture is allowed to react for 30 minutes and then stored in concentrated form at 4 degrees C. until use.

D. Analyte Binding Assay

The analyte binding assay overall is similar to that described in Example 5 above with two exceptions; 1) a streptavidin/biotin tracer nucleic acid conjugate is constructed at a 1:3 stoichiometry to increase the sensitivity of the assay and 2) the analyte to be detected in the sample medium is not an antibody, but a virus particle.

Into each of at least six tubes is placed 1 HIV binding bead. Assays are run in at least duplicate; two marked as S1 and S2 respectively for sample medium, two marked P1 and P2 for positive control and two marked N1 and N2 for negative control. The beads are washed with TBS and 145 ul of TBS with 10% BSA and either 5 ul of negative control serum, positive control serum or sample serum. The beads are allowed to react for 4 hours with the sample/test fluid and then the beads are washed three times with TBS and 0.5% Tween-20 (TBST) in order to remove unreacted antibodies.

The beads are then treated with a 125 ul of 1:1500 dilution of biotin labeled rat anti-HIV antibody made as directed above and incubated for 2 hours. The HIV binding beads are then washed three times with TBS and 0.5% Tween-20

(TBST) in order to remove unreacted goat antibodies. A 125 ul volume of a 1:2000 dilution of the stock streptavidin/biotin tracer nucleic acid conjugate (1:3 stoichiometry) is added to the separated HIV beads and allowed to react for 40 minutes. The HIV beads are then washed three times with TBST and three times with TBS. The beads are now ready for a polymerase detection reaction. The streptavidin/biotin polynucleotide conjugate is double stranded, the polymerase detection assay is run for 180 minutes and interpreted as in Example 1.

Example 8
Assay Method with a Biotinylated Rat Monoclonal Anti-HIV Polymerized Polynucleotide Assay Reagent In this example multiple polynucleotide sequences are attached to a single ligand in a polymer or matrix fashion. The ligand is a biotinylated monoclonal antibody specific for HIV proteins.

A. Preparation of Assay Components

The biotin rat monoclonal anti-HIV conjugate and immobilized analyte binding reagent, polyclonal human anti HIV immunoglobulin, are prepared as described in Example 7. The biotin conjugated polynucleotide is made as follows.

The commercially available plasmid, pBluescript SK+/− (Stratagene) modified with a Sph I/Bgl II adaptor as described in Example 1 or other suitable plasmid containing one or more RNA phage promoters is constructed. Milligram quantities of plasmid DNA are then purified and subjected to the following series of treatments. one milligram of purified plasmid is completely cleaved to generate approximately 400 pmoles of overhanging 3' ends with Sph I endonuclease, phenol extracted, ethanol precipitated. It is redissolved in a reaction medium comprising 250 units of nuclease free terminal transferase enzyme, 2.0 nmoles of 5-([N-biotinyl]-3-amino-allyl)-2'-deoxyuridine 5'-triphosphate, 2.0 mM $CoCl_2$, 100 mM potassium cacodylate (pH 7.2), 0.2 mM dithiothreitol, heated to 37 degrees C. and incubated for 1 hour.

5-([N-biotinyl]-3- amino-allyl)-2'-deoxyuridine 5'-triphosphate is a competitive inhibitor of terminal transferase and results in the addition of 1 to 2 biotin labeled oligonucleotides per nucleic acid strand, with two strands per template. The mixture is phenol extracted, ethanol precipitated, redissolved in aqueous solution, and loaded onto a column of Bio-Gel P-100™ preequilibrated with water. The double stranded 3' biotinylated heteropolymer nucleic acids free of BSA are collected in the void volume, pooled as a stock solution. Sodium azide is added to the stock solution to a final concentration of 0.1% sodium azide and stored a 4 degrees ready for use in analyte binding assay.

B. Analyte Binding Assay

The assay overall is similar to that described in Example 7 above with two exceptions; 1) a streptavidin is not preincubated with the biotin tracer nucleic acid conjugate to form a single streptavidin/biotin tracer nucleic acid reagent component but the streptavidin/template nucleic acid complex is formed by stepwise, sequential incubations and washes of tracer template and streptavidin and 2) biotin tracer nucleic acid conjugate comprises at least one biotin per 3' end of the double stranded tracer nucleic acid template.

Into each of at least six tubes is placed 1 HIV binding bead made as directed in Example 7. Assays are run in at least duplicate; two marked as S1 and S2 respectively for sample medium, two marked P1 and P2 for positive control and two marked N1 and N2 for negative control. The beads are washed with TBS and 145 ul of TBS with 10% BSA and either 5 ul of negative control serum, positive control serum or sample serum. The beads are allowed to react for 4 hours with the sample/test fluid and then the beads are washed three times with TBS and 0.5% Tween-20 (TBST) in order to remove unreacted antibodies.

The beads are then treated with a 125 ul of 1:1500 dilution of biotin labeled rat anti-HIV antibody made as directed above and incubated for 2 hours. The HIV binding beads are then washed three times with TBS and 0.5% Tween-20 (TBST) in order to remove unreacted goat antibodies. A 125 ul volume of a 1:2000 dilution of the stock tracer nucleic acid conjugated to biotin on both 3' ends is added to the separated HIV binding beads and allowed to react for 20 minutes. The HIV binding beads are then washed three times with TBST. A 125 ul volume of a 1:2000 dilution of the stock tracer nucleic acid conjugated to biotin on both 3' ends is added to the separated HIV binding beads and allowed to react for 20 minutes. The HIV binding beads are then washed three times with TBST. A 125 ul volume of a streptavidin solution (2.5 mg/ml, w/v) diluted 1:1000 in TBST is added to each HIV binding bead and allowed to react for 20 minutes. The HIV binding beads are then washed three times with TBST.

A second 125 ul volume of a 1:2000 dilution of the stock tracer nucleic acid conjugated to biotin on both 3' ends is added to the separated HIV binding beads and allowed to react for 20 minutes. The HIV binding beads are then washed three times with TBST. A second 125 ul volume of a streptavidin solution (2.5 mg/ml, w/v) diluted 1:1000 in TBST is added to each HIV binding bead and allowed to react for 20 minutes. The HIV binding beads are then washed three times with TBST.

A third 125 ul volume of a 1:2000 dilution of the stock tracer nucleic acid conjugated to biotin on both 3' ends is added to the separated HIV binding beads and allowed to react for 20 minutes. The HIV binding beads are then washed three times with TBST and three times with TBS. The successive stepwise incubation of streptavidin and biotinylated tracer template effective constitutes a type of template amplification cycle.

The streptavidin/biotin nucleic acid conjugate is now in an insoluble three dimensional polymer or matrix due to the 4 biotin binding sites on streptavidin and the biotin group of the 3' end of the double stranded tracer nucleic acid. The amplification of the amount of immobilized or insoluble template indirectly attached to the support can be increased by repetitive cycles of; incubation of support with bifunctional tracer template, wash support, incubation of support with streptavidin or other multivalent biotin binding agent, wash support, incubation of support with tracer template, wash etc. These cycles can be repeated multiple times to increase the sensitivity of the analyte binding assay prior to initiating a polymerase detection reaction. The polymerase detection assay is run with each HIV binding bead for 90 minutes and interpreted as in Example 1.

Example 9
Assay Method with a Polynucleotide Assay Reagent Containing Two Ligands: a Biotinylated Rat Monoclonal Anti-HIV and a Biotinylated Mouse Monoclonal Anti-Hepatitis B Surface Antigen In this example a polynucleotide assay reagent is prepared by attaching at least two ligands, a biotinylated rat monoclonal antibody specific for HIV proteins and a biotinylated mouse monoclonal antibody specific for Hepatitis B surface antigen (HbsAg) through a biotin/streptavidin bridge for use in a heterogeneous analyte binding assay to detect the presence of a analyte or analytes, a HIV particle or Hepatitis B virus particle.

A. Biotin Monoclonal Conjugates

A biotinylated rat monoclonal antibody (Zymed) that reacts with HIV strains LAV, ARV and HTLV III is prepared as directed in Example 7. A mouse monoclonal antibody (Zymed) that reacts with Hepatitis B surface antigen (HbsAg) is dialyzed in 0.1M bicarbonate buffer, pH 8.4 at a concentration of 10 mg/ml. Biotin-N-Hydroxysuccinimide (BNHS) is dissolved at a concentration of 10 mg/ml in dimethylformamide immediately before use. The dissolved BNHS is added to the dialyzed protein solution at a ratio of 1:10 (BHNS/protein, w/w) while slowly mixing. The mixture is incubated for 1 hour at room temperature and then dialyzed extensively in TBS. The concentrated biotin labeled mouse anti-HbsAg immunoglobulin is stored at 4 degrees C.

B. Immobilized First Analyte binding Agents

To 8 grams of nonporous spherical Hydrazide Beads (Pierce) 5 ml of 12.5% glutaraldehyde solution (2.5 ml of 25% glutaraldehyde diluted to 5 ml with 0.1M sodium phosphate, pH 7) is added. The beads are then placed on a rocker with gentle shaking for 2 hours, washed with 200 ml of water in a Buchner funnel followed by a wash with 40 ml of 0.1 sodium phosphate, pH 6.0.

The activated beads are then added to a solution of 5 mg of polyclonal human IgG purified by affinity chromatography using a mixture of HIV and the HBV adw/ayr proteins ( see Example 2 above) as an absorbent from HIV/HBV reactive plasma a human immunoglobulin source (Scripps Laboratories) and is dialyzed in 0.1M sodium phosphate, pH 6.0 to equilibrium. After mixing, 2 mg of sodium cyanoborohydride is added to the mixture with gentle shaking for 15 hours to reduce Schiff bases. The HIV/HBV binding coupled polystyrene beads are washed with 200 ml of 0.1M sodium phosphate, pH 6.0 followed by a wash with 50 ml of sodium bicarbonate.

To the HIV/HBV binding hydrazide beads is added 10 ml 0.1M sodium bicarbonate containing about 1 mg of sodium borohydride with gentle shaking for 15 minutes. The HIV/HBV binding beads are then washed with 200 ml of sodium carbonate followed by 200 ml of water and then air dried. The air dry HIV/HBV binding coupled beads are then blocked with a 1.0% solution of casein (Sigma C-5890) in phosphate buffered saline for 20 minutes maximum. The beads are then rinsed with 200 ml TBS buffer with 0.1% sodium azide twice, air dried and stored at 4 degrees in a moisture proof pouch prior to use.

C. Streptavidin/Biotin Conjugated Tracer Nucleic Acid

In TBS buffer with 0.1% sodium azide are combined 0.4 nmoles of streptavidin and 1.2 nmoles of tracer nucleic acid biotinylated with up to two biotin labeled nucleotides at a single end made as directed in Example 5 above. The mixture is allowed to react for 30 minutes and then stored in concentrated form at 4 degrees C. until use.

D. Analyte Binding Assay

The assay overall is similar to that described in Example 7 above with two exceptions; 1) two types of first analyte binding agents, polyclonal human anti-HIV and polyclonal human anti-HBV are employed for analyte capture and 2) two second analyte binding agents, monoclonal biotinylated rat anti-HIV and monoclonal biotinylated mouse anti-HBV are employed to report the presence of at least one of two analytes, HIV proteins and/or HBV proteins.

Into each of at least six tubes is placed 1 HIV/HBV binding bead made as directed. Assays are run in at least duplicate; two marked as S1 and S2 respectively for sample medium, two marked P1 and P2 for positive control and two marked N1 and N2 for negative control. The beads are washed with TBS and 145 ul of TBS with 10% BSA and either 5 ul of negative control serum, positive control serum or sample serum. The beads are allowed to react for 4 hours with the sample/test fluid and then the beads are washed three times with TBS and 0.5% Tween-20 (TBST) in order to remove unreacted antibodies.

The beads are then treated with 70 ul of a 1:750 dilution of biotin labeled rat anti-HIV monoclonal antibody and a 70 ul of a 1:750 dilution of a biotin labeled mouse anti-HBV monoclonal antibody made as directed above and incubated for 2 hours. The HIV/HBV binding beads are then washed three times with TBS and 0.5% Tween-20 (TBST) in order to remove unreacted goat antibodies. A 125 ul volume of a 1:2000 dilution of the stock streptavidin/biotin tracer nucleic acid conjugate (1:3 stoichiometry) is added to the separated HIV/HBV beads and allowed to react for 40 minutes. The HIV/HBV beads are then washed three times with TBST and three times with TBS. The beads are ready for a polymerase detection reaction. The streptavidin/biotin tracer nucleic acid conjugate is double stranded with a functional promoter. The polymerase detection assay is run for 180 minutes and interpreted as in Example 1.

Example 10

Assay Method with a Polynucleotide Assay Reagent Containing a Monoclonal Anti-SV40 and a Modified Single-Stranded Ribo/deoxyribopolynucleotide An important aspect of this particular polynucleotide assay reagent is that it is composed of a DNA sequence identical to part of the DNA contained within an analyte particle, such as an SV40 particle. This provides a mechanism to increase the sensitivity of the assay. The analyte specific primers and polymerase extension reactions employed copy both the polynucleotide and the analyte DNA.

A. Monoclonal Antibody Reacting With SV40

The outer capsid of SV40 virus is composed of repeating units of the major surface protein VP1 which makes up 70% of the viron protein. SV40 virus DNA (Life Technologies, Inc.) is transfected into CV1 cells (Life Technologies, Inc.) by calcium phosphate method of Graham. From lytic foci of the initial transfection a virus is plaque purified and then confluent CV1 cell cultures are infected with 5 plaque forming units per cell to produce a virus rich supernatant fluid. Virus is purified according to the method of Barban.

The monoclonal antibodies useful in the present invention are obtained by the process discussed by Milstein using milligram amounts of the above purified SV40 virus as an immunogen. A monoclonal antibody clone having an affinity for SV40 of greater than 107 liters/mole is selected, expanded and milligram amounts of mouse anti-SV40 monoclonal is purified from either ascites fluid or tissue culture fluid by protein A chromatography.

B. Preparation of Oxidized Single Stranded Heteropolymer Tracer DNA

The synthesis of ribo/deoxyribose DNA heteropolymers is performed as described in Example 2 with the exception that the oligonucleotide synthesis employs oxidation by sulfur instead of with iodine/water/lutidine/tetrahydrofuran. This DNA synthesis modification produces a thiophosphodiester bond between nucleotide sugars. The following three oligonucleotides designated as oligonucleotide 1,2 and 3 respectively have the 5' phosphate of the heteropolymer blocked or protected from exonuclease digestion by aminoalkylation with 1,2-diaminoethane as described in Example 2:

1) 5'GAATTCCTTTGCCTAAATTTAAATGAG-GACTTAACCTGTGGAAATATTTTGAT-GTGGGAArC 3', 2) 5'TTAATACGACTCACTATAGGGATG
TTCCCACATCAAAATATTTC 3', 3) 5'GAATTCCTTTCG 3'.

The single ribose ring (rC) at the 3' end of the largest purified oligonucleotide is ready for oxidation. Approximately 0.8 nmoles 3' end ribo labeled heteropolymer is dissolved in water and the solution adjusted to pH 7.0 at 0 degrees C. Sodium periodate (1.0 nmoles) is added and the solution is allowed to stand in the dark at 4 degrees C. The reaction is stopped by the addition of ethylenediol (0.10 nmoles) and the reaction is loaded onto a column of Bio-Gel P-30™ preequilibrated with water. The oxidized heteropolymer nucleic acids now labeled with a dialdehyde functionality are collected in the void volume, pooled and ready for conjugation with analyte or analyte binding agent.

C. Preparation of Monoclonal Antibody Tracer Nucleic Acid

Ten milligrams of affinity purified plain unconjugated mouse monoclonal antibody directed against SV40 in 2 ml of TBS is dialyzed against 0.125 N-ethyl morpholine acetate buffer, pH 8.4, containing 1 mM EDTA until equilibrium. The dialyzed mouse monoclonal is then reacted with 40 ug of terminal aldehyde moiety attached to the oxidized 3' end of the single stranded heteropolymer tracer DNA synthesized as described in Example 2. The reaction proceeds with gentle mixing for 10 minutes and then sodium borohydride is added in 5 fold excess over aldehyde concentration and the solution is allowed to stand for 35 minutes.

The mixture is then applied to a Bio-Gel P-200™ column preequilibrated in TBS. The mouse monoclonal anti-SV40 nucleic acid conjugate elutes in the void volume of the gel filtration column. The void volume fractions are pooled and stored in concentrated form at 4 degrees C. with 0.1% sodium Azide.

D. Immobilized Anti-SV40 Monoclonal Antibody

Eight grams of nonporous spherical Hydrazide Beads (Pierce) are activated as described in Example 1 above. The activated beads are then added to a solution of 5 mg of mouse anti-SV40 monoclonal antibody which has been dialyzed in 0.1M sodium phosphate, pH 6.0 to equilibrium. After mixing, 2 mg of sodium cyanoborohydride is added to the mixture with gentle shaking for 15 hours to reduce Schiff bases. The SV40 binding polystyrene beads are washed with 200 ml of 0.1M sodium phosphate, pH 6.0 followed by a wash with 50 ml of sodium bicarbonate.

To the SV40 binding hydrazide beads is added 10 ml 0.1M sodium bicarbonate containing about 1 mg of sodium borohydride with gentle shaking for 15 minutes. The SV40 binding beads are then washed with 200 ml of sodium carbonate followed by 200 ml of water and then air dried. The air dried SV40 binding beads are then blocked with a 1.0% solution of casein (Sigma C-5890) in phosphate buffered saline for 20 minutes maximum. The beads are then rinsed with 200 ml TBS buffer with 0.1% sodium azide twice, air dried and stored at 4 degrees in a moisture-proof pouch prior to use.

E. Analyte Binding Assay

Into each of at least six tubes is placed 1 SV40 binding bead for assays run in at least duplicate; two marked as S1 and S2 respectively for sample medium from a tissue culture flask suspected of being infected with SV40 virus, two marked P1 and P2 for positive control and two marked N1 and N2 for negative control. The beads are washed with TBS and 145 ul of TBS with 10% BSA and either 5 ul of negative control tissue culture fluid, positive control tissue culture fluid or test culture fluid. The beads are allowed to react for 2 hours with the test/sample fluid and then the beads are washed three times with TBS and 0.5% Tween-20 (TBST)

in order to remove unreacted sample material. The beads are then treated with a 125 ul of a 1:2000 dilution of the mouse anti-SV40 tracer nucleic acid conjugate and incubated for 1 hour. The beads are then washed three times with TBST and three times with TBS. The beads are now ready for a polymerase detection reaction.

Into each tube is placed 150 ul of transcription/polymerization buffer which consists of 25 mM potassium phosphate, 10 mM magnesium chloride and 100 mM sodium chloride at pH7.5, 3 nmoles of the above 2nd oligonucleotide, (5'TTAATACGACTCACTATAGGGAT GTTCCCACATCAAAATATTTC 3'), 12 nmoles of dATP, 22 nmoles of dCTP, 10 nmoles TTP and 19 nmoles of dGTP. All tubes are heated to 95 degrees for five minutes and allowed to cool to 37 degrees over 15 minutes. Ten units of Klenow fragment of E. coli DNA polymerase 1 are added and the temperature is maintained for 30 minutes resulting in the synthesis of the first complementary strand. In the positive control sample the 5' end of the first complementary strand is covalently attached to the second oligonucleotide which thus attaches ½ of a promoter sequence at the 5' end of the strand.

Into each tube is now added 3 nmoles of the above 3rd oligonucleotide, (5'GAATTCCTTTCG 3'). All tubes are heated to 95 degrees for five minutes and allowed to cool to 37 degrees over 15 minutes. Ten units of Klenow fragment of E. coli DNA polymerase 1 are added and the temperature is maintained for 30 minutes resulting in the synthesis of the second complementary strand. The 3' end of the second strand now contains the other ½ of the promoter. Together the new double stranded complex includes a replica of the tracer nucleic acid attached to a functional promoter that can now (with the promoter now affixed to a template replica) utilize RNA polymerase. Because oligonucleotides two and three are not overlapping, no replica is made unless there is a template and RNA polymerase can be legitimately employed to detect the presence of template. The samples are then analyzed by running a polymerase detection reaction as performed and interpreted in Example 1.

The template used in this example does not contain any internal RNA promoter sequences. However, by employing an oligonucleotide with tracer specific sequences at its 3' end and also half a promoter sequence at its 5' end and performing a polymerase extension reaction in one direction followed by the annealing of a target specific oligonucleotide to the 3' end of the newly synthesized strand and a second reverse polymerization/reaction, a RNA polymerase promoter sequence can be added to sequences from both the tracer template and the analyte template.

The series of annealing an oligonucleotide to a template and polymerization/extension from the oligonucleotide can be repeated multiple times to amplify the initial template immobilized to the support. In addition, the transcripts generated from the newly created promoter which generally do not include the promoter sequence, can also be converted into templates with promoters by using the appropriately designed primer set. The process is analogous to that used to generate the initial template with the prominent exception, that utilizing an RNA transcript as a template to synthesize DNA requires the use of a special DNA polymerase, reverse transcriptase.

The cycle of making transcripts, converting transcripts into templates with promoters and making another set of transcripts is an effective way to amplify the original tracer nucleic acid and thereby increase the sensitivity of the analyte binding assay. Again it is noteworthy that nucleotide analogues may be employed as substrates in the amplification type polymerase reactions as well as the "designated" polymerase detection reaction since no polymerization will occur unless a template is present. Because the template is Immobilized only by virtue of the analyte interacting with the insoluble first analyte binding agent, the integral value of all polymerization reactions is informative.

In addition to analytes such as viruses or bacteria, the analyte binding assay using a polymerase detection reaction as an indicator can be adapted to detect analytes as large as T lymphocytes. With the appropriate standards the analyte binding assay can be adapted to determine parameters which are usually limited to such complex techniques as automated flow cytometry.

Initially a calibration curve is generated for a given set of reagents and conditions of a polymerase detection reaction using information obtained from another source such as flow cytometry. When a calibration curve has been established with a given set of components under a particular set of conditions, the polymerase assay coupled to the appropriate analyte binding agents can be used to determine such parameters as total T cell count, absolute Helper T cell number as well as Helper/Suppressor T cell ratio.

Example 11
Assay Method with an Immobilized Monoclonal Anti-SV40

The analyte is an infectious agent having polynucleotide material. Therefore, the analyte itself can serve as a polynucleotide reporter.

A. Analyte Binding Assay

Into each of at least six tubes is placed 1 SV40 binding bead for assays run in at least duplicate; two marked as S1 and S2 respectively for sample medium from a tissue culture flask suspected of being infected with SV40 virus, two marked P1 and P2 for positive control and two marked N1 and N2 for negative control. The beads are washed with TBS and 145 ul of TBS with 10% BSA and either 5 ul of negative control tissue culture fluid, positive control tissue culture fluid or test culture fluid. The beads are allowed to react for 2 hours with the test/sample fluid. The beads are washed three times with TBS and 0.5% Tween-20 (TBST) and three times with TBS in order to remove unreacted sample material. The beads are now ready for a polymerase detection reaction.

Into each tube is placed 150 ul of transcription/polymerization buffer which consists of 25 mM potassium phosphate, 10 mM magnesium chloride and 100 mM sodium chloride at pH7.5, 3 nmoles of the above 2nd oligonucleotide, (5'TTAATACGACTCACTATAGGGATG TTCCCACATCAAAATATTTC 3'), 12 nmoles of dATP, 22 nmoles of dCTP, 10 nmoles TTP and 19 nmoles of dGTP. All tubes are heated to 95 degrees for five minutes and allowed to cool to 37 degrees over 15 minutes. Ten units of Klenow fragment of $E.$ $coli$ DNA polymerase 1 are added and the temperature is maintained for 30 minutes resulting in the synthesis of the first complementary strand if the virus and its nucleic acid template is present in sample. In the positive control sample or a sample with virus present the 5' end of the first complementary strand is covalently attached to the second oligonucleotide which thus attaches ½ of a promoter sequence at the 5' end of the strand.

Into each tube is now added 3 nmoles of the above 3rd oligonucleotide, (5'GAATTCCTTTCG 3'). All tubes are heated to 95 degrees for five minutes and allowed to cool to 37 degrees over 15 minutes. Ten units of Klenow fragment of $E.$ $coli$ DNA polymerase 1 are added and the temperature is maintained for 30 minutes resulting in the synthesis of the second complementary strand. The 3' end of the second strand now contains the other ½ of the promoter. Together the new double stranded complex includes a replica of the tracer nucleic acid attached to a functional promoter that can now (with the promoter now affixed to a template replica) utilize RNA polymerase. Because oligonucleotides two and three are not overlapping, no replica is made unless there is a template and RNA polymerase can be legitimately employed to detect the presence of any virus template. The samples are then analyzed by running a polymerase detection reaction as performed and interpreted in Example 1.

Example 12
Assay Method for Detecting a Complementary Oligonucleotide Sequence with a Polynucleotide Assay Reagent In this example the analyte is a oligonucleotide sequence complementary to the polynucleotide sequence of the assay reagent. Specifically, a portion of the SV40 DNA is used to analyze the DNA of virus particles isolated by plaque purification.

A. Immobilized Analyte Binding Reagent

Two portions of ten micrograms of Virus preparation, are phenol extracted, ethanol precipitated and redissolved in a 15 ul of a medium comprising 60 mM $NaCl_2$, 10 mM Tris-HCL (pH7.5), 10 mM $MgCl_2$, 6 mM 2-mercaptoethanol, 100 ug/ml bovine serum albumin. To one portion of the mixture ten units of the restriction endonuclease Pvu II, (New England Biolabs, Inc.) is added and reacted for 1 hour at 37 degrees C. The two samples are then electrophoresed and transferred to a nitrocellulose sheet as described by Southern.

B. Biotin Labeled Analyte Conjugate

Biotin is attached to the 3' end of the analyte or probe nucleic acid by the use of terminal transferase as described in Example 5. One microgram of the SV40 DNA described in Example 10 is cleaved to completion with the restriction endonuclease Pst I to generate two fragments of SV40 viral DNA with four 3' extending ends. This material is then phenol extracted and ethanol precipitated. It is redissolved in a reaction medium comprising 25 units of nuclease free terminal transferase enzyme, 0.20 nmoles of 5-([N-biotinyl] -3-amino-allyl)-2'-deoxyuridine 5'-triphosphate, 2.0 mM $CoCl_2$, 100 mM potassium cacodylate (pH 7.2), 0.2 mM dithiothreitol, heated to 37 degrees C. and incubated for 1 hour. 5-([N-biotinyl]-3-amino-allyl)-2'-deoxyuridine 5'-triphosphate is a competitive inhibitor of terminal transferase and results in the addition of 1 to 2 biotin labeled oligonucleotides per 3' end. The analyte is then heat denatured and quick chilled just prior to using as a probe.

Since the analyte is being used as a probe and not as a template for a polymerization reaction other methods of incorporating a biotin analyte into the analyte nucleic acid are tolerated. These include incorporation of biotin into polynucleotide strands by nick-translation described by Rigby or random priming described by Feinberg.

The streptavidin/biotin conjugated tracer nucleic acid is made as described in Example 5.

C. Analyte Binding Assay

The filter is wetted with a prehybridization solution comprising 1.0M NaCl and 1% SDS and incubated at 65 degrees C. for 1 to 3 hours. The prehybridization fluid is replaced with a hybridization solution comprised of 10% destran sulfate, 1.0M NaCl, 1% SDS, 100 ug/ml denatured sheared salmon sperm DNA and the denatured biotin labeled Pst I fragments of SV40 DNA. The filter is incubated with the hybridization solution for at least 12 hours at 65 degrees C. and then washed with a solution comprising 300 mM NaCl, 20 mM $Na_2PO_4$, pH 7.4, 2 mM EDTA and 1% SDS for 15 minutes at 65 degrees C. This first wash material is removed and a second wash with the following solution is initiated: 15 mM NaCl, 1.0 mM Na$_2$PO$_4$, pH 7.4, 0.1 mM EDTA and 1% SDS. The second wash is allowed to incubate for 30 minutes at 65 degrees C. and is removed. A third wash is initiated with the same solution and is allowed to incubate for 30 minutes at 65 degrees C. The third wash is removed and the filter is air dried. The air dried filter is then blocked with a 1.0% solution of casein (Sigma C-5890) in TBS for 20 minutes maximum. The filter is then rinsed with 200 ml TBS buffer with 0.1% sodium azide twice, air dried and stored at 4 degrees in a moisture proof pouch prior to use.

The filter is now placed into another clear plastic bag and washed with TBS. The filter is then treated with 10 ml of a 1:2000 dilution of the streptavidin tracer nucleic acid conjugated and incubated for 30 minutes. The filter is then washed three times with TBST and three times with TBS and is ready for a polymerase detection reaction as described in Example 6. After the polymerization detection assay, the filter shows 1 lane with a single band about 5 kilobases in size. The other lane representing the Pvu II digestion shows three bands at the following sizes in basepairs: 2002, 1790 and 1446.

Example 13
Assay Method for Detecting an Analyte on a Nitrocellulose Blot by a Strepavidin-Polynucleotide Assay Reagent The analyte binding agent in this example is defined as the reactive molecule biotin-N-hydroxysuccinimide ester as described by Hofmann. 10 ug/well equivalent of HIV (Scripps Laboratories) is electrophoresed on a 12% polyacrylamide slab gel in the presence of sodium dodecylsulfate (SDS). The protein material is electrophoretically transferred to a nitrocellulose sheet, as described by Towbin.

After transfer a 0.5 cm strip of the sheet air is dried and then incubated with 1:50 (v/v) dilution of Biotinyl-N-hydroxysuccinimide ester (5 mg/ml) dissolved in dimethylformamide diluted in TBS. The material is allowed to react for 30 minutes and the strip is rinsed 3 times with TBS. The strip is now placed into another clear plastic bag and washed with TBS. The filter is then treated with 10 ml of a 1:2000 dilution of the streptavidin tracer nucleic acid, conjugated (see Example 5) and incubated for 30 minutes. The filter is then washed three times with TBST and three times with TBS and is ready for a polymerase detection reaction as described in Example 6. After the polymerization detection assay, the strip shows staining of the representative proteins of HIV from each of the following sizes; p18, p24, p31, gp41, p51, p55, p65, gp120 and gp160.

Example 14
Heterogenous Assay Method with a Polynucleotide Assay Reagent Containing Theophylline In this example a polynucleotide is directly attached to the small ligand, theophylline. In particular, the promoter of the polynucleotide is in a ligand proximal region.

A. Theophylline-Polynucleotide Assay Reagent

The following 5' phosphorylated oligonucleotide containing phosphorothioates is synthesized as de scribed in Example 10 and designated as oligo A:

5'PO$_4$TAATACGACTCACTATAGGGCGAATTCGAG-CTCGGTACCCGGGGATCCTCTAGAGTC-GACCTG3'.

The complementary oligonucleotide designated as oligo B containing phosphorothioates is also synthesized with the following DNA sequence:

5' CAGGTCGACTCTAGAGGATCCCCGGG-TACCGAGCTCGAATTCGCCCTATAGT-GAGTCGTATTA 3'.

It is a preferred embodiment of the invention to use phosphorothioate linkages since theophylline is ordinarily measured in serum which often contains nucleases. The oligo A is converted to the 5'-aminoethylphosphoroamidate analogue by reacting with 1,2-diaminoethane in the presence of 1-ethyl-3-(N,N-dimethylamino) isopropyl carbodiimide hydrochloride (EDC) and N-methylimidazole for 18 hours as described by Chollet. The 5'-aminoethylphosphoroamidate analogue is designated as oligo A-NEN.

The A-NEN oligo converted into the theophyllinetracer nucleic acid conjugate by the reaction of the lactam of 8-(3-carboxypropyl)- 1,3-dimethylxanthine with the primary amine of the A-NEN oligo. Fifty milligrams of the lactam of 8-(3-carboxypropyl)-1,3-dimethylxanthine is dissolved in 5 ml of dimethylacetimide and 0.1 micromoles in two milliters of oligo A-NEN and is dialyzed to equilibrium against 0.01 4'hydroxyazobenzene-2-carboxylic acid. A fifty microliter aliquot of the 8-(3-carboxypropyl)-1,3-dimethylxanthine lactam is added to the A-NEN oligo solution and stirred at 4 degrees C. for 10 minutes. A second fifty microliter aliquot of the 8-(3-carboxypropyl)-1,3-dimethylxanthine lactam is added to the A-NEN solution and stirred for an additional 10 minutes at 4 degrees C. increasing the reaction temperature to 22 degrees for 30 minutes. The material is then placed on a Bio-ge™ P-30 column preequilibrated in TBS. The void material is pooled and then further purified by affinity chromatography.

An anti-theophylline monoclonal antibody (Medix Biotech) is coupled to Affi-Gel® 702 (Bio-Rad) according to the manufacturer's instructions to make an anti-theophylline column. The pool material in TBS is loaded on the anti-theophylline column, washed with 3 column volumes of TBS and eluted with 2M NaI. The eluted material is dialyzed against TBS until equilibrium.

To the theophylline-NEN-oligo A heteropolymer is added an equimolar amount of oligo B and the solution is heated to 95 degrees C. for 10 minutes and gradually cooled over 20 minutes to 65 degrees C. The mixture is incubated for an additional 45 minutes and then slowly cooled to 8 degrees C. over a 2 hours period. The theophylline-tracer nucleic acid conjugate is now double stranded and sodium azide is added to a final concentration of 0.1% and the material is stored at 4 degrees C. until use.

B. Immobilized Theophylline Binding Agent

The amount of immobilized analyte binding reagent can significantly affect the sensitivity of an assay in a competitive format. In addition, the inherent responsiveness of the polymerase detection reaction permits both dilutions of sample and assay components to reduce the cost per assay. A mouse IgG$_1$ anti-theophylline monoclonal is immobilized to hydrazine beads as directed in Example 10 with the following exception. The amount of analyte binding agent that is immobilized per bead is empirically determined depending on the usual concentration of the analyte in the sample medium to be analyzed. The initial antibody concentration used to immobilize the mouse anti-theophylline monoclonal is 0.001 milligram/bead instead of an average 0.1 milligram of antibody per bead. Otherwise the immobilization process of the monoclonal antibody is identical to that described in Example 10.

C. Analyte Binding Assay

The theory of competitive assays is well established. The analyte present in the sample medium will compete with the theophylline-polynucleotide for the immobilized analyte binding sites on the support. If analyte is present in the sample medium, it will displace the theophylline-polynucleotide reagent from the support and release it into the residual assay fluid. The residual assay fluid is subjected to a polymerization detection reaction to measure the amount of analyte initially present in the sample medium.

Stock calibration samples of theophylline at the following concentrations are made up in control human serum having no detectable xanthine compounds present: 25 milligrams/liter, 20 milligrams/liter, 15 milligrams/liter, 10 milligrams/liter, 5 milligrams/liter, and 1 milligram/liter. Into each of at least 14 tubes is placed 1 theophylline binding bead for assays run in at least duplicate; two marked as Si and S2 respectively for a 1:1000 dilution of sample serum of an individual suspected of being treated with theophylline; a set of six pairs marked P1$a$ and P1$b$ through P25$a$ and P25$b$ for 1:1000 dilutions of calibration controls representing 1 milligram/liter through 25 milligrams/liter respectively and two marked N1 and N2 for a 1:1000 dilution of a negative control. All dilutions are done with TBST.

Into each tube is placed 1 nmole of the theophylline-tracer nucleic acid conjugate and 200 ul of each of the diluted specimens into their respectively marked tubes. Each mixture is incubated at 37 degrees C. for two hours and the beads are removed from the mixture separating the residual assay fluid from the support. The residual assay fluid is now ready for analysis by a polymerase detection reaction.

Into a new set of respectively labeled tubes is placed 100 ul aliquots of each residual assay fluid and 100 ul of 2× transcription/polymerization buffer and the samples are then analyzed by running a polymerase detection reaction as performed in Example 1. The analysis is performed by plotting a linear regression on the calibration controls and then comparing the average signal intensity of the unknown sample with the corresponding value from the linear regression. Should the calibration curve not produce a linear signal over the range of dilutions chosen, another range of dilutions is chosen to provide a dynamic linear range. Usually, theophylline levels greater than 25 milligrams/liter are toxic, and reporting a toxic value of greater than or equal to 25 milligrams/liter provides adequate clinical information. If an absolute analyte concentration is required, for example for forensic purposes, a dilution of the sample is performed and the assay is rerun.

Example 15
Homogenous Assay Method with a Polynucleotide Assay Reagent Containing Theophylline In this example a polynucleotide is directly attached to a ligand, theophylline, for use in a competitive format for a homogeneous assay using a polymerase detection reaction to measure the presence of analyte in a sample.

A. Analyte Binding Assay

The three components required for a competitive format of a homogeneous assay are the polynucleotide assay reagent, an analyte binding agent, and a detection component. The same polynucleotide assay reagent as described in Example 14 is employed in Example 15. However the analyte binding agent, a mouse IgG$_1$ anti-theophylline monoclonal antibody, differs from that of Example 15 in that the antibody is not attached to an insoluble support.

Stock calibration samples of theophylline at the following concentrations are made up in control human serum having no detectable xanthine compounds present: 25 milligrams/liter, 20 milligrams/liter, 15 milligrams/liter, 10 milligrams/liter, 5 milligrams/liter, and 1 milligram/liter. Into each of at least 14 tubes is placed 50 ng theophylline binding monoclonal antibody for assays run in at least duplicate; two marked as S1 and S2 respectively for a 1:1000 dilution of samples serum of an individual suspected of being treated with theophylline; a set of six pairs marked P1$a$ and P1$b$ through P25$a$ and P25$b$ for 1:1000 dilutions of calibration controls representing 1 milligram/liter through 25 milligrams/liter respectively and two marked N1 and N2 for a 1:1000 dilution of a negative control. All dilutions are done with TBS.

Into each tube is placed 1 nmole of the theophylline-tracer nucleic acid conjugate and 200 ul of each of the diluted specimens into their respectivly marked tubes. Each mixture is incubated at 37 degrees C. for two hours and a 100 microliter aliquot of the binding assay fluid is removed from each mixture.

Into a new set of respectively labeled tubes is placed 10 ul aliquots from each binding assay fluid and 100 ul of 2× transcription/polymerization buffer and the samples are then analyzed by running a polymerase detection reaction as performed in Example 1. The analysis is performed by plotting a linear regression on the calibration controls and then comparing the average signal intensity of the unknown sample with the corresponding value from the linear regression.

Should the calibration curve not produce a linear signal over the range of dilutions chosen, another range of dilutions is chosen to provide a dynamic linear range. Usually, theophylline levels greater than 25 milligrams/liter are toxic, and reporting a toxic value of greater than or equal to 25 milligrams/liter provides adequate clinical information. Again as in the heterogeneous assay, if an absolute analyte concentration is required, for example for forensic purposes, a dilution of the sample is performed and the assay is rerun.

Although the invention has been described with respect to particular embodiments, it will be appreciated that various changes and modifications can be made without departing from the invention.

It is claimed:

1. An immunoassay method for detecting an analyte in a liquid sample, where the analyte is either an antigen-specific antibody or an antigen capable of competing with an antigen ligand for binding to an antigen-specific antibody, said method comprising contacting the sample with binding reagent means including a polynucleotide assay reagent composed of an antigen ligand and a polynucleotide attached to the ligand and containing an initiation region adjacent the ligand, where said ligand is effective to bind with an antigen-specific antibody to form an immunocomplex in which said initiation region is blocked by the formation of the immunocomplex, said antigen-specific antibody being either an analyte, or a component of the binding reagent means where the analyte is an antigen capable of competing with the antigen ligand for binding to the antigen-specific antibody, reacting the polynucleotide assay reagent after said contacting with a polymerase and nucleotide triphosphates in a reaction mixture under conditions effective to copy the polynucleotide, with utilization of said nucleotide triphosphates, and production of cleavage products containing a phosphate or pyrophosphate moiety, only if the polynucleotide's initiation region is not blocked, and after said reacting, assaying said reaction mixture for the presence of a cleavage product containing a phosphate or pyrophosphate moiety, where the assayed amount of said cleavage product is related to the amount of analyte in the sample.

2. The method of claim 1, wherein said initiation region in the assay reagent includes a selected polynucleotide sequence, and said reacting includes adding to the reaction mixture an oligonucleotide primer which is complementary to said selected initiation region sequence, and said reacting is carried out under annealing conditions which allow the primer to anneal to the initiation region only if such is not blocked.

3. The method of claim 1, wherein said initiation region in the assay reagent includes a promoter region, and said polymerase which is capable of copying the polynucleotide after binding to the promoter, and said reacting is carried out under conditions in which the polymerase binds to the promoter only if such is not blocked.

4. The method of claim 3, wherein the polymerase is selected form the group consisting of DNA-dependent DNA polymerases, DNA-dependent RNA polymerases, reverse transcriptases and replicases.

5. The method of claim 1, wherein the nucleotide triphosphate include nucleotide triphosphate species which are fluorescence labeled at the gamma phosphate, and said assaying includes measuring a fluorescence-labeled phosphate or pyrophosphate moiety.

6. An immunoassay kit for detecting an analyte in a liquid sample, where the analyte is either an antigen-specific antibody or an antigen capable of competing with an antigen ligand for binding to an antigen-specific antibody, said kit comprising binding reagent means including a polynucleotide assay reagent composed of an antigen ligand and a polynucleotide attached to the ligand and containing an initiation region adjacent the ligand, and effective, where said ligand is effective to bind with an antigen-specific antibody to form an immunocomplex which in which said initiation region is blocked by the formation of the immunocomplex, said antigen-specific antibody being either the analyte to be detected, or a component of the binding reagent means where the analyte to be detected is an antigen capable of competing with the antigen ligand for binding to the antigen-specific antibody, polymerase reagents effective to copy the polynucleotide in said assay reagent only if its initiation region is not blocked, and detection reagents for detecting the presence of a cleavage product containing a phosphate or pyrophosphate moiety in a reaction mixture, where the detected amount of said cleavage product is related to the amount of analyte in the sample.

7. The kit of claim 6, wherein said initiation region in the assay reagent includes a selected polynucleotide sequence, and said polymerase reagents include an oligonucleotide which is complementary to said selected initiation region sequence.

8. The kit of claim 6, wherein said assay reagent includes a promoter region, and said polymerase is capable of copying the polynucleotide after binding to the promoter, but only if the initiation region is unblocked.

9. The kit of claim 8, wherein the polymerase is selected form the group consisting of DNA-dependent DNA polymerases, DNA-dependent RNA polymerases, reverse transcriptases and replicases.

10. The kit of claim 6, wherein the polymerase reagents include nucleotide triphosphate species which are fluorescence labeled at the gamma phosphate, and said detection reagents include reagents for measuring a fluorescence-labeled phosphate or pyrophosphate moiety.

* * * * *